US006455140B1

(12) United States Patent
Whitney et al.

(10) Patent No.: US 6,455,140 B1
(45) Date of Patent: *Sep. 24, 2002

(54) VISIBLE MIRROR FILM GLITTER

(75) Inventors: Leland R. Whitney, St. Paul; Andrew J. Ouderkirk, Woodbury, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/582,928

(22) PCT Filed: Jan. 13, 1999

(86) PCT No.: PCT/US99/00741

§ 371 (c)(1),
(2), (4) Date: Jul. 5, 2000

(87) PCT Pub. No.: WO99/36477

PCT Pub. Date: Jul. 22, 1999

(51) Int. Cl.[7] .................................................. B23B 7/02
(52) U.S. Cl. ...................... 428/212; 428/323; 428/402; 428/403; 428/407
(58) Field of Search ................... 428/402, 403, 428/407, 212, 323

(56) References Cited

U.S. PATENT DOCUMENTS

| ,540,768 A | 6/1895 | Western ........................ 40/477 |
| RE24,906 E | 12/1960 | Ulrich ..................... 526/322.5 |
| 3,124,639 A | 3/1964 | Kahn .......................... 359/488 |
| 3,549,405 A | 12/1970 | Schrenk et al. ............. 428/142 |
| 3,565,985 A | 2/1971 | Schrenk et al. ........ 264/171.27 |
| 3,610,729 A | 10/1971 | Rogers ....................... 359/488 |
| 3,711,176 A | 1/1973 | Alfrey, Jr. et al. .......... 359/359 |
| 3,764,067 A | 10/1973 | Coffey et al. .................... 239/1 |
| 3,801,429 A | 4/1974 | Schrenk et al. ............. 428/392 |
| 3,860,036 A | 1/1975 | Newmann, Jr. .............. 138/45 |
| 4,181,752 A | 1/1980 | Martens et al. ............. 427/516 |
| 4,249,011 A | 2/1981 | Wendling ................ 548/319.5 |
| 4,310,584 A | * 1/1982 | Copper ....................... 428/212 |
| 4,329,384 A | 5/1982 | Vesley et al. ............... 428/41.3 |
| 4,356,429 A | 10/1982 | Tang .......................... 313/503 |

(List continued on next page.)

FOREIGN PATENT DOCUMENTS

| EP | 0 718 380 | 6/1996 |
| JP | HEI-SEI 2-33004 | 4/1988 |
| WO | WO 95/27919 | 4/1995 |
| WO | WO 95/17303 | 6/1995 |
| WO | WO 95/17691 | 6/1995 |
| WO | WO 95/17692 | 6/1995 |
| WO | WO 95/17699 | 6/1995 |
| WO | WO 96/19347 | 6/1996 |
| WO | WO 97/01440 | 1/1997 |
| WO | WO 97/01774 | 1/1997 |
| WO | WO 97/30136 | 8/1997 |
| WO | WO 97/32226 | 9/1997 |
| WO | WO 99/36248 | 7/1999 |
| WO | WO 99/36262 | 7/1999 |
| WO | WO 99/36478 | 7/1999 |

OTHER PUBLICATIONS

Weber et al., "Giant Birefringent Optics in Multilayer Polymer Mirrors", Science, vol. 287, Mar. 31, 2000, pp. 2451–2456.

Schrenk et al., Nanolayer polymeric optical films, Tappi Journal, pp. 169–174, Jun., 1992.

*Primary Examiner*—Leszek Kiliman
(74) *Attorney, Agent, or Firm*—Dale A. Bjorkman; Stephen C. Jensen

(57) ABSTRACT

Glitter, at least a portion of which, comprise visible mirror film. The glitter is useful in any of a variety of ways, including in loose form, attached to the surface of a substrate, in a dispersible combination, or present in a matrix material ranging, for example, from liquids, such as water and alcohols, to gels, such as silicone and glycenol, to hard, rigid materials such as plastics, particle board and fiberglass.

47 Claims, 10 Drawing Sheets

U.S. PATENT DOCUMENTS

| | | | |
|---|---|---|---|
| 4,415,615 A | 11/1983 | Esmay et al. | 428/41.5 |
| 4,446,305 A | 5/1984 | Rogers et al. | 528/348 |
| RE31,780 E | 12/1984 | Cooper et al. | 428/212 |
| 4,520,189 A | 5/1985 | Rogers et al. | 528/331 |
| 4,521,588 A | 6/1985 | Rogers et al. | 528/363 |
| 4,525,413 A | 6/1985 | Rogers et al. | 428/212 |
| 4,605,592 A | 8/1986 | Paquette et al. | 428/334 |
| 4,710,536 A | 12/1987 | Klingen et al. | 524/493 |
| 4,717,511 A | 1/1988 | Koroscil | 252/700 |
| 4,720,426 A | 1/1988 | Englert et al. | 428/344 |
| 5,043,851 A | 8/1991 | Kaplan | 362/34 |
| 5,086,088 A | 2/1992 | Kitano et al. | 522/170 |
| 5,146,707 A | 9/1992 | Nichols | 43/42.53 |
| 5,188,760 A | 2/1993 | Hikmet et al. | 252/299.01 |
| 5,211,878 A | 5/1993 | Reiffenrath et al. | 252/299.63 |
| 5,232,635 A | 8/1993 | Van Moer et al. | 252/700 |
| 5,235,443 A | 8/1993 | Barnik et al. | 349/194 |
| 5,247,190 A | 9/1993 | Friend et al. | 257/40 |
| 5,269,995 A | 12/1993 | Ramanathan et al. | 264/173.12 |
| 5,294,657 A | 3/1994 | Melendy et al. | 524/270 |
| 5,316,703 A | 5/1994 | Schrenk | 264/1.34 |
| 5,319,478 A | 6/1994 | Fijnfschilling et al. | 349/181 |
| 5,383,954 A | 1/1995 | Craig | 106/31.08 |
| 5,389,324 A | 2/1995 | Lewis et al. | 264/173.12 |
| 5,407,603 A | 4/1995 | Morrison | 252/519.3 |
| 5,409,783 A | 4/1995 | Tang | 428/690 |
| 5,448,404 A | 9/1995 | Schrenk et al. | 359/584 |
| 5,469,019 A | 11/1995 | Mori | 313/509 |
| 5,486,935 A | 1/1996 | Kalmanash | 35/194 |
| 5,486,949 A | 1/1996 | Schrenk et al. | 359/498 |
| 5,508,585 A | 4/1996 | Butt | 313/509 |
| 5,554,450 A | 9/1996 | Shi et al. | 428/690 |
| 5,598,059 A | 1/1997 | Sun et al. | 313/509 |
| 5,612,820 A | 3/1997 | Schrenk et al. | 359/498 |
| 5,629,055 A | 5/1997 | Revol et al. | 428/1.31 |
| 5,686,979 A | 11/1997 | Weber et al. | 349/96 |
| 5,699,188 A | 12/1997 | Gilbert et al. | 359/584 |
| 5,721,603 A | 2/1998 | De Vaan et al. | 349/194 |
| 5,744,534 A | 4/1998 | Ishiharada et al. | 524/442 |
| 5,751,388 A | 5/1998 | Larson | 349/96 |
| 5,767,935 A | 6/1998 | Ueda et al. | 349/112 |
| 5,770,306 A | 6/1998 | Suzuki et al. | 428/328 |
| 5,783,120 A | 7/1998 | Ouderkirk et al. | 264/134 |
| 5,793,456 A | 8/1998 | Broer et al. | 349/98 |
| 5,808,794 A | 9/1998 | Weber et al. | 359/487 |
| 5,825,542 A | 10/1998 | Cobb, Jr. et al. | 359/487 |
| 5,825,543 A | 10/1998 | Ouderkirk et al. | 359/494 |
| 5,882,774 A * | 3/1999 | Jonza | 428/212 |
| 5,940,149 A | 8/1999 | Hikmet et al. | 349/5 |
| 5,962,114 A | 10/1999 | Jonza et al. | 428/212 |
| 5,965,247 A | 10/1999 | Jonza et al. | 428/212 |
| 6,012,820 A * | 1/2000 | Weber | 362/19 |
| 6,080,467 A * | 6/2000 | Weber | 428/212 |
| 6,082,876 A * | 7/2000 | Hanson | 362/293 |
| 6,096,375 A | 8/2000 | Ouderkirk et al. | 427/163.1 |
| 6,107,447 A | 8/2000 | Kreuder et al. | 528/310 |
| 6,141,149 A | 10/2000 | Carlson et al. | 359/500 |
| 6,185,039 B1 | 2/2001 | Allen et al. | 359/495 |
| 6,207,260 B1 | 3/2001 | Wheatley et al. | 428/212 |
| 6,299,979 B1 | 10/2001 | Neubauer et al. | 428/407 |

\* cited by examiner

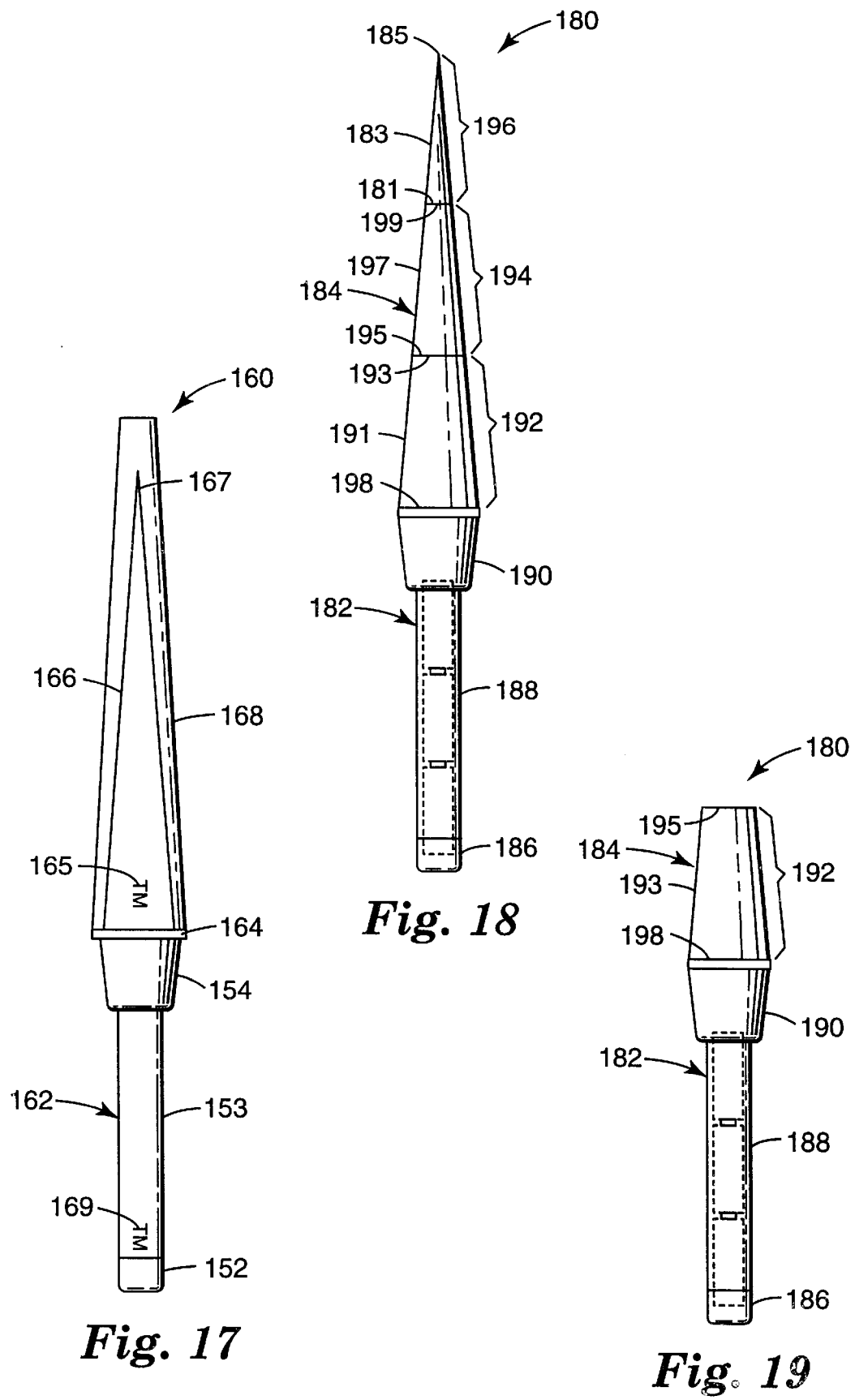

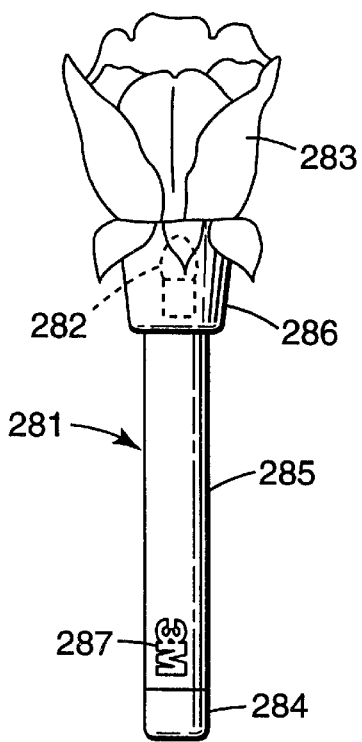
Fig. 26
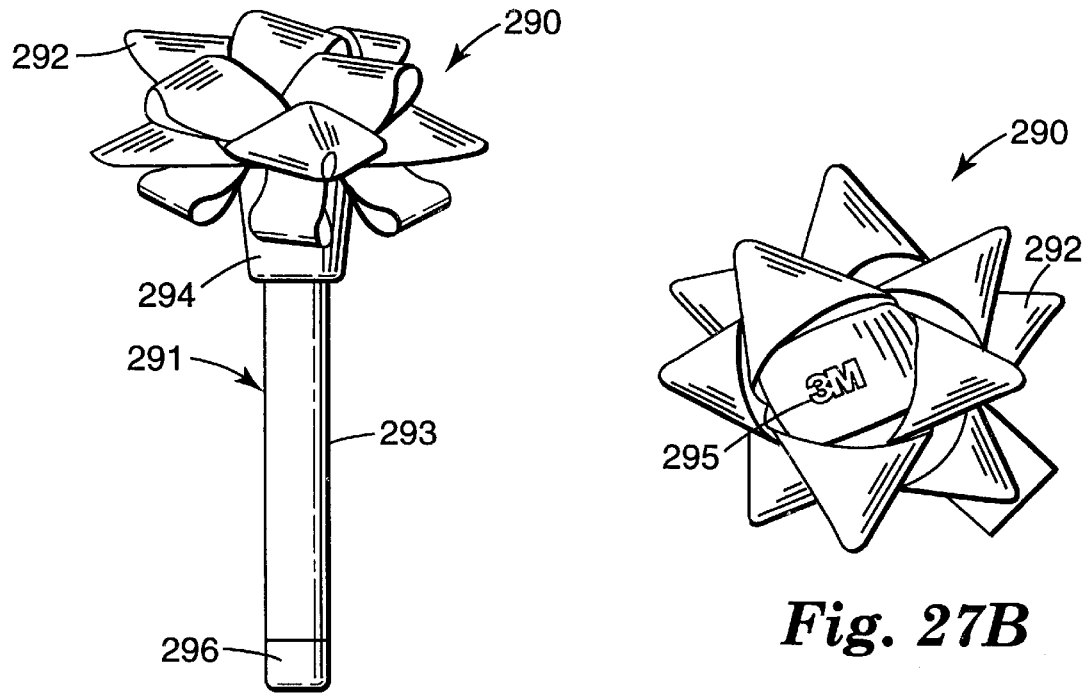
Fig. 27A
Fig. 27B

VISIBLE MIRROR FILM GLITTER

CROSS REFERENCE TO RELATED APPLICATIONS

The present national application claims priority to international application PCT/US99/00741 which was filed Jan. 13, 1999 and published in English as PCT publication WO 99/36477, and claims priority as a continuation-in-part to U.S. application Ser. No. 09/006,293, filed Jan. 13, 1998, now abandoned.

FIELD OF THE INVENTION

The present invention relates to glitter having desirable and/or unique optical characteristics.

BACKGROUND OF THE INVENTION

Glitter, which is a plurality of particles (i.e., a pieces or fragments of a material) having a regular or irregular periphery, is known in forms that include light reflecting or light refracting material (see, e.g., U.S. Pat. No. RE 31,780 (Cooper et al.), U.S. Pat. No. 3,764,067 (Coffey et al.), U.S. Pat. No. 4,310,584 (Cooper et al.), and U.S. Pat. No. 5,294,657 (Melendy et al.)). Materials useful as glitter include particles of metal (e.g., aluminum, copper, silver, gold, and brass), particles of transparent or colored, solid organic materials (e.g., poly(ethylene terephthalate), polymethacrylate, and poly(vinylbutyral)), and particles of metal coated film or paper (e.g., aluminum coated poly (ethylene terephthalate) film). Glitter may be clear and/or be provided in a variety of colors (e.g., silver, gold, blue, red, etc.), or mixtures thereof; and may be provided in a variety of shapes (e.g., circles, squares, rectangles, triangles, diamonds, stars, symbols, alphanumerics (i.e., letters and/or numbers), or mixtures of different shapes.

Glitter may be used in loose form (i.e., non-agglomerated, flowable) adhered to or embedded in a solid material, or dispersed in a liquid. In loose form, for example, glitter may be thrown into the air to create a decorative visual display during a festive occasion, such as a party or parade, or spinkled onto a surface (including hair). In another aspect, glitter is commonly adhered to the surface of, or embedded in, articles (e.g., jewelry, clothing, toys and novelties, art work, and ornaments) to enhance their visual appearance. Glitter is also dispersed in a liquid to provide a visual effect (e.g., globes having a winter scene with simulated snow flakes), or to enhance the appearance of a coating (e.g., paints (e.g., automotive paints and hobby paints), glue, and fingernail polish).

Metallic glitter, which is the among the most reflective types of glitter, is frequently preferred for a variety of end uses. The use of metallic glitter is not, however, without disadvantage. Some reflective metals used in glitter such as silver and gold are relatively expensive. Others, such as copper or aluminum may corrode or oxidize when exposed to air and/or water. Hence, metal containing glitters are relatively expensive, due to the inherent cost of the metal and/or because they require the addition of a protective coating which increases the cost and complexity of producing the glitter. In addition, solid metal glitters (i.e., glitter comprising solid particles or flakes of metal) may abrade equipment (e.g., spray guns, mixers, and extruders) used in the manufacture glitter or glitter-containing products. Further, solid metal glitters have a higher specific gravity than typical coating formulations, thus causing the glitter to settle to the bottom of the coating container.

Conventional plastic glitters avoid some of the infirmities associated with metal glitters, but have additional infirmities of their own. Thus, many prior art plastic glitters, especially those based on absorbing dyes or pigments, exhibit reflectivities that are much lower than those observed with metallic glitters. Other plastic glitters are unavailable in certain colors, due to the inflexibility of their method of manufacture. Still other plastic glitters reflect light in a primarily diffuse (as opposed to specular) manner. These features, alone or in combination, result in a glitter that lacks vibrancy and is not eye-catching.

There is thus a need in the art for a plastic glitter or glitter composition that is inexpensive, highly reflective, available in a wide variety of colors, and catching to the eye. These and other needs are met by the glitters of the present invention, as hereinafter described.

SUMMARY OF THE INVENTION

The present invention provides glitter (particles) comprising film disclosed herein.

One preferred glitter according to the present invention is glitter comprising film comprising a plurality of alternating layers of at least a first and second polymeric material, wherein at least one of the first or second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05.

Glitter according to the present invention may be in any of a variety of desired shapes (e.g., circles, squares, rectangles, triangles, diamonds, stars, alphanumerics, symbols, characters (e.g., comic, television, movie, etc.), other polygons (e.g., hexagons), and mixtures of at least two different shapes) and sizes (including mixtures of two or more different sizes). Typically, at least a portion of the glitter has particle sizes (i.e., maximum particle dimension) of up to about 1.25 cm (0.5 inch), more typically less than about 10 mm, or even less than about 3 mm. In another aspect, at least a portion of the glitter typically has particle sizes ranging from about 50 micrometers to about 3 mm; for some uses preferably from about 100 micrometers to about 3 mm. Larger particles sizes (i.e., up to about 1.25 cm (0.5 inch)) of glitter according to the present invention may be preferred for use as confetti.

In another aspect, the thickness of film (e.g., visible mirror film) comprising glitter according to the present invention is typically less than about 125 micrometers, more typically less than 75 micrometer, and preferably less than 50 micrometers. For some applications, such as paints (e.g., automotive paints), thicknesses of even 15 micrometers may also be useful. In another aspect, the thickness of the film is selected such that it is less than or equal to 25% of the minimum planar dimension of the glitter particle formed from the film. For example, for a circular glitter particle having a diameter of about 1 mm, the preferred film thickness would be less than or equal to about 0.25 mm.

Glitter according to the present invention may be used or provided in any of a variety ways, including in loose form, attached to the surface of a substrate, in a dispersible combination, or present in a matrix material ranging, for example, from liquids, such as water and alcohols, to gels, such as silicone and glycerol, to hard, rigid materials such as plastics, particle board, and fiberglass. Examples of other matrix materials include putties or molding clays, rubbers, adhesives (e.g., glue sticks), crayons, and paper and cardboard.

In one embodiment wherein the glitter is incorporated into a matrix material (e.g., a cross-linked polymeric material), a composite article comprises glitter according to the present invention dispersed (e.g., uniformly or non-uniformly) within a translucent (including transparent) matrix material. In another embodiment wherein the glitter is incorporated into a matrix material, a composite article comprises glitter according to the present invention dispersed within a matrix material, wherein at least a portion of the glitter according to the present invention is observable by a viewer of the composite material comprising the matrix material and the glitter. In the latter example, the matrix material need not be translucent (i.e., can be opaque) provided that glitter is at the outer surface of the matrix material such that at least a portion of the glitter according to the present invention is observable by a viewer of the article.

In another aspect, the present invention provides an article or composition comprising a substrate, a matrix disposed on the substrate, and a plurality of glitter according to the present invention disposed in the matrix.

Articles incorporating glitter according to the present invention may, for example, have the glitter uniformly or non-uniformly (including randomly) dispersed therein and/or thereon, as well have some areas with the glitter uniformly or non-uniformly dispersed therein and/or thereon, and other areas wherein it is non-uniformly or uniformly, respectively, dispersed therein and/or thereon. Further, the glitter may be present such that there are concentration gradients of glitter.

Glitter according tot he present invention can be used, for example, to interact with electromagnetic radiation (e.g., visible light) to create desirable, interesting, and/or unique visual effects.

Visible mirror film used in the present invention has the advantage that it can be constructed as a multilayer optical film which has relatively low absorption of incident light, as well as high reflectivity for off-axis as well as normal light rays. Another advantage is unlike metal based reflectors, for example, multilayer optical films do not tarnish in water or high humidity conditions.

Glitter converted from visible mirror film has unusually visually pleasing properties when viewed "in the flop" (i.e., when viewed at such an angle that the specular reflection is not causing a glint or a sparkle). In the flop, the visible mirror film, especially at smaller glitter sizes such as 0.2 mm (0.008 inch) and smaller, simply disappears into the background, without appearing dark or grey, thereby giving a dirty appearance to the background. Other glitters, especially metallic glitters, in the flop look dark thereby giving a dirty appearance.

BRIEF DESCRIPTION OF THE DRAWINGS

FIG. 17 is a side view of another hand-holdable toy light tube according to the present invention;

FIG. 18 is a side view of another hand-holdable toy light tube according to the present invention in an extended position;

FIG. 19 is a side view of the hand-holdable toy light tube of FIG. 18 in a retracted position;

FIG. 26 is a side view of another hand-holdable novelty article according to the present invention;

FIG. 27A is a side view of another hand-holdable novelty article according to the present invention;

FIG. 27B is a top view of the novelty article of FIG. 27A.

DETAILED DESCRIPTION

Figure 1:
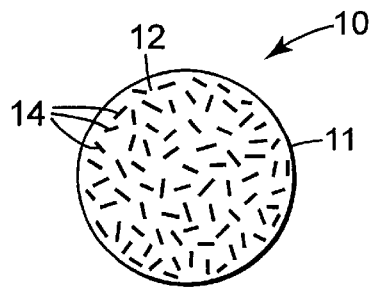
FIGS. 1–7 are perspective views of various exemplary toy balls according to the present invention.

Glitter according to the present invention may be in any of a wide variety of shapes or sizes. In loose form, the glitter can be used, for example, as confetti and thrown into the air to create a visual display or effect. Typically, the layers within the glitter according to the present invention are preferably essentially parallel.

Preferred visible mirror films for use in the present invention are described in applications having U.S. Ser. No. 08/402,041, filed Mar. 10, 1995, now U.S. Pat. No. 5,882,774 Ser. No. 08/494,366, filed Jun. 26, 1995 now U.S. Pat. No. 6,080,467, and Ser. No. 09/006,601, filed Jan. 13, 1998 now abandoned. A special case of some mirror and polarizing (optical) films are certain color shifting films.

Visible mirror films are birefringent polymeric films having particular relationships between the refractive indices of successive layers for light polarized along mutually orthogonal in-plane axes (the x-axis and the y-axis) and along an axis perpendicular to the in-plane axis (the z-axis).

A visible mirror film comprises a plurality of alternating layers of at least a first and second polymeric material wherein at least one of the first or second polymeric materials is birefringent; and wherein the difference in indices of refraction of the first and second polymeric materials for visible light polarized along both mutually orthogonal in-plane axes of the film is at least 0.05; and wherein the difference in indices of refraction of the first and second polymeric materials for visible light polarized along a third axis normal to the plane of the film is less than about 0.05.

In an ideal mirror, the difference in refractive index criteria for the in-plane axes apply equally in any direction in the film plane. Material and processing considerations are made to maximize these refractive index difference. The spectral bandwidth of preferred interest is typically between 400 nm to 700 nm.

Various process considerations are important in making high quality optical films (including mirrors). The process conditions used to make each film will depend in part on the particular resin system used and the desired optical properties of the final film. The following description is intended as an overview of those process considerations common to many resin systems used in making the coextruded optical films useful for the present invention.

Material Selection for the Films

Regarding the materials from which the preferred films (i.e., the preferred visible mirror films, as well as preferred polarizer and color shifting films) are to be made, there are several conditions which must be met that are common to all multilayer optical films of this invention. First, these films comprise at least two distinguishable polymers. The number is not limited. and three or more polymers may be advantageously used in particular films. Second, one of the two required polymers, referred to as the "first polymer", must have a stress optical coefficient having a large absolute value. In other words, it must be capable of developing a large birefringence when stretched. Depending on the application, this birefringence may be developed between two orthogonal directions in the plane of the film, between one or more in-plane directions and the direction perpendicular to the film plane, or a combination of these. Third, the first polymer must be capable of maintaining this birefringence after stretching, so that the desired optical properties are imparted to the finished film. Fourth, the other required polymer, referred to as the "second polymer", must be chosen so that in the finished film, its refractive index, in at least one direction, differs significantly from the index of refraction of the first polymer in the same direction. Because polymeric materials are dispersive, that is, the refractive indices vary with wavelength, these conditions must be considered in terms of a spectral bandwidth of interest.

Other aspects of polymer selection depend on specific applications. For polarizing films, it is advantageous for the difference in the index of refraction of the first and second polymers in one film-plane direction to differ significantly in the finished film, while the difference in the orthogonal film-plane index is minimized. If the first polymer has a large refractive index when isotropic, and is positively birefringent (that is, its refractive index increases in the direction of stretching), the second polymer will be chosen to have a matching refractive index, after processing, in the planar direction orthogonal to the stretching direction, and a refractive index in the direction of stretching which is as low as possible. Conversely, if the first polymer has a small refractive index when isotropic, and is negatively birefringent, the second polymer will be chosen to have a matching refractive index, after processing, in the planar direction orthogonal to the stretching direction, and a refractive index in the direction of stretching which is as high as possible.

Alternatively, it is possible to select a first polymer which is positively birefringent and has an intermediate or low refractive index when isotropic, or one which is negatively birefringent and has an intermediate or high refractive index when isotropic. In these cases, the second polymer may be chosen so that, after processing, its refractive index will match that of the first polymer in either the stretching direction or the planar direction orthogonal to stretching. Further, the second polymer will be chosen such that the difference in index of refraction in the remaining planar direction is maximized, regardless of whether this is best accomplished by a very low or very high index of refraction in that direction.

One means of achieving this combination of planar index matching in one direction and mis-matching in the orthogonal direction is to select a first polymer which develops significant birefringence when stretched, and a second polymer which develops little or no birefringence when stretched, and to stretch the resulting film in only one planar direction. Alternatively, the second polymer may be selected from among those which develop birefringence in the sense opposite to that of the first polymer (negative—positive or positive—negative). Another alternative method is to select both first and second polymers which are capable of developing birefringence when stretched, but to stretch in two orthogonal planar directions, selecting process conditions, such as temperatures, stretch rates, post-stretch relaxation, and the like, which result in development of unequal levels of orientation in the two stretching directions for the first polymer. and levels of orientation for the second polymer such that one in-plane index is approximately matched to that of the first polymer, and the orthogonal in-plane index is significantly mismatched to that of the first polymer. For example. conditions may be chosen such that the first polymer has a biaxially oriented character in the finished film, while the second polymer has a predominantly uniaxially oriented character in the finished film.

The foregoing is meant to be exemplary, and it will be understood that combinations of these and other techniques may be employed to achieve the polarizing film goal of index mismatch in one in-plane direction and relative index matching in the orthogonal planar direction.

Different considerations apply to a reflective, or mirror, film. Provided that the film is not meant to have some polarizing properties as well, refractive index criteria apply equally to any direction in the film plane, so it is typical for the indices for any given layer in orthogonal in-plane directions to be equal or nearly so. It is advantageous, however, for the film-plane indices of the first polymer to differ as greatly as possible from the film-plane indices of the second polymer. For this reason, if the first polymer has a high index of refraction when isotropic, it is advantageous that it also be positively birefringent. Likewise, if the first polymer has a low index of refraction when isotropic, it is advantageous that it also be negatively birefringent. The second polymer advantageously develops little or no birefringence when stretched, or develops birefringence of the opposite sense (positive—negative or negative—positive), such that its film-plane refractive indices differ as much as possible from those of the first polymer in the finished film. These criteria may be combined appropriately with those listed above for polarizing films if a mirror film is meant to have some degree of polarizing properties as well.

Color shifting films can be regarded as special cases of mirror and polarizing films. Thus, the same criteria outlined above apply. The perceived color is a result of reflection or polarization over one or more specific bandwidths of the spectrum. The bandwidths over which a multilayer film of the current invention is effective will be determined primarily by the distribution of layer thicknesses employed in the optical stack(s), but consideration must also be given to the wavelength dependence, or dispersion, of the refractive indices of the first and second polymers. It will be understood that the same rules apply to the infrared and ultraviolet wavelengths as to the visible colors.

Absorbance is another consideration. For most applications, it is advantageous for neither the first polymer nor the second polymer to have any absorbance bands within the bandwidth of interest for the film in question. Thus, all incident light within the bandwidth is either reflected or transmitted. However, for some applications, it may be useful for one or both of the first and second polymer to absorb specific wavelengths, either totally or in part.

Polyethylene 2,6-naphthalate (PEN) is frequently chosen as a first polymer for films of the present invention. It has a large positive stress optical coefficient, retains birefringence effectively after stretching, and has little or no absorbance within the visible range. It also has a large index of refraction in the isotropic state. Its refractive index for polarized incident light of 550 nm wavelength increases when the plane of polarization is parallel to the stretch direction from about 1.64 to as high as about 1.9. Its birefringence can be increased by increasing its molecular orientation which, in turn, may be increased by stretching to greater stretch ratios with other stretching conditions held fixed.

Other semicrystalline naphthalene dicarboxylic polyesters are also suitable as first polymers. Polybutylene 2,6-Naphthalate (PBN) is an example. These polymers may be homopolymers or copolymers, provided that the use of comonomers does not substantially impair the stress optical coefficient or retention of birefringence after stretching. The term "PEN" herein will be understood to include copolymers of PEN meeting these restrictions. In practice, these restrictions imposes an upper limit on the comonomer content, the exact value of which will vary with the choice of comonomer(s) employed. Some compromise in these properties may be accepted, however, if comonomer incorporation results in improvement of other properties. Such properties include but are not limited to improved interlayer adhesion, lower melting point (resulting in lower extrusion temperature), better rheological matching to other polymers in the film, and advantageous shifts in the process window for stretching due to change in the glass transition temperature.

Suitable comonomers for use in PEN, PBN or the like may be of the diol or dicarboxylic acid or ester type. Dicarboxylic acid comonomers include but are not limited to terephthalic acid, isophthalic acid, phthalic acid, all isomeric naphthalenedicarboxylic acids (2,6-, 1,2-, 1,3-, 1,4-, 1,5-, 1,6-, 1,7-, 1,8-, 2,3-, 2,4-, 2,5-, 2,7-, and 2,8-), bibenzoic acids such as 4,4'-biphenyl dicarboxylic acid and its isomers, trans-4,4'-stilbene dicarboxylic acid and its isomers, 4,4'-diphenyl ether dicarboxylic acid and its isomers, 4,4'-diphenylsulfone dicarboxylic acid and its isomers, 4,4'-benzophenone dicarboxylic acid and its isomers, halogenated aromatic dicarboxylic acids such as 2-chloroterephthalic acid and 2,5-dichloroterephthalic acid, other substituted aromatic dicarboxylic acids such as tertiary butyl isophthalic acid and sodium sulfonated isophthalic acid, cycloalkane dicarboxylic acids such as 1,4-cyclohexanedicarboxylic acid and its isomers and 2,6-decahydronaphthalene dicarboxylic acid and its isomers, bi- or multi-cyclic dicarboxylic acids (such as the various isomeric norbornane and norbornene dicarboxylic acids, adamantane dicarboxylic acids, and bicyclo-octane dicarboxylic acids), alkane dicarboxylic acids (such as sebacic acid, adipic acid, oxalic acid, malonic acid, succinic acid, glutaric acid, azelaic acid, and dodecane dicarboxylic acid.), and any of the isomeric dicarboxylic acids of the fused-ring aromatic hydrocarbons (such as indene, anthracene, pheneanthrene, benzonaphthene, fluorene and the like). Alternatively, alkyl esters of these monomers, such as dimethyl terephthalate, may be used.

Suitable diol comonomers include but are not limited to linear or branched alkane diols or glycols (such as ethylene glycol, propanediols such as trimethylene glycol, butanediols such as tetramethylene glycol, pentanediols such as neopentyl glycol, hexanediols, 2,2,4-trimethyl-1,3-pentanediol and higher diols), ether glycols (such as diethylene glycol, triethylene glycol, and polyethylene glycol), chain-ester diols such as 3-hydroxy-2,2-dimethylpropyl-3-hydroxy-2,2-dimethyl propanoate, cycloalkane glycols such as 1,4-cyclohexanedimethanol and its isomers and 1,4-cyclohexanediol and its isomers, bi- or multicyclic diols (such as the various isomeric tricyclodecane dimethanols, norbornane dimethanols, norbornene dimethanols, and bicyclo-octane dimethanols), aromatic glycols (such as 1,4-benzenedimethanol and its isomers, 1,4-benzenediol and its isomers, bisphenols such as bisphenol A, 2,2'-dihydroxy biphenyl and its isomers, 4,4'-dihydroxymethyl biphenyl and its isomers, and 1,3-bis(2-hydroxyethoxy)benzene and its isomers), and lower alkyl ethers or diethers of these diols, such as dimethyl or diethyl diols.

Tri- or polyfunctional comonomers, which can serve to impart a branched structure to the polyester molecules, can also be used. They may be of either the carboxylic acid, ester, hydroxy or ether types. Examples include, but are not limited to, trimellitic acid and its esters, trimethylol propane, and pentaerythritol.

Also suitable as comonomers are monomers of mixed functionality, including hydroxycarboxylic acids such as parahydroxybenzoic acid and 6-hydroxy-2-naphthalenecarboxylic acid, and their isomers, and tri- or polyfunctional comonomers of mixed functionality such as 5-hydroxyisophthalic acid and the like.

Polyethylene terephthalate (PET) is another material that exhibits a significant positive stress optical coefficient, retains birefringence effectively after stretching, and has little or no absorbance within the visible range. Thus, it and its high PET-content copolymers employing comonomers listed above may also be used as first polymers in some applications of the current invention.

When a naphthalene dicarboxylic polyester such as PEN or PBN is chosen as first polymer, there are several approaches which may be taken to the selection of a second polymer. One preferred approach for some applications is to select a naphthalene dicarboxylic copolyester (coPEN) formulated so as to develop significantly less or no birefringence when stretched. This can be accomplished by choosing comonomers and their concentrations in the copolymer such that crystallizability of the coPEN is eliminated or greatly reduced. One typical formulation employs as the dicarboxylic acid or ester components dimethyl naphthalate at from about 20 mole percent to about 80 mole percent and dimethyl. terephthalate or dimethyl isophthalate at from about 20 mole percent to about 80 mole percent, and employs ethylene glycol as diol component. Of course, the corresponding dicarboxylic acids may be used instead of the esters. The number of comonomers which can be employed in the formulation of a coPEN second polymer is not limited.

Suitable comonomers for a coPEN second polymer include but are not limited to all of the comonomers listed above as suitable PEN comonomers, including the acid, ester, hydroxy, ether, tri- or polyfunctional, and mixed functionality types.

Often it is useful to predict the isotropic refractive index of a coPEN second polymer. A volume average of the refractive indices of the monomers to be employed has been found to be a suitable guide. Similar techniques well-known in the art can be used to estimate glass transition temperatures for coPEN second polymers from the glass transitions of the homopolymers of the monomers to be employed.

In addition, polycarbonates having a glass transition temperature compatible with that of PEN and having a refractive index similar to the isotropic refractive index of PEN are also useful as second polymers. Polyesters, copolyesters, polycarbonates, and copolycarbonates may also be fed together to an extruder and transesterified into new suitable copolymeric second polymers.

It is not required that the second polymer be a copolyester or copolycarbonate. Vinyl polymers and copolymers made from monomers such as vinyl naphthalenes, styrenes, ethylene, maleic anhydride, acrylates, acetates, and methacrylates may be employed. Condensation polymers other than polyesters and polycarbonates may also be used. Examples include: polysulfones, polyamides, polyurethanes, polyamic acids, and polyimides. Naphthalene groups and halogens such as chlorine, bromine and iodine are useful for increasing the refractive index of the second polymer to a desired level. Acrylate groups and fluorine are particularly useful in decreasing refractive index when this is desired.

It will be understood from the foregoing discussion that the choice of a second polymer is dependent not only on the intended application of the multilayer optical film in question, but also on the choice made for the first polymer, and the processing conditions employed in stretching. Suitable second polymer materials include but are not limited to polyethylene naphthalate (PEN) and isomers thereof (such as 2,6-, 1,4-, 1,5-, 2,7-, and 2,3-PEN), polyalkylene terephthalates (such as polyethylene terephthalate, polybutylene terephthalate, and poly-1,4-cyclohexanedimethylene terephthalate), other polyesters, polycarbonates, polyarylates, polyamides (such as nylon 6, nylon 11, nylon 12, nylon 4/6, nylon 6/6, nylon 6/9, nylon 6/10, nylon 6/12, and nylon 6/T), polyimides (including thermoplastic polyimides and polyacrylic imides), polyamide-imides, polyetheramides, polyetherimides, polyaryl ethers (such as polyphenylene ether and the ring-substituted polyphenylene oxides), polyarylether ketones such as polyetheretherketone ("PEEK"), aliphatic polyketones (such as copolymers and terpolymers of ethylene and/or propylene with carbon dioxide), polyphenylene sulfide, polysulfones (including polyethersulfones and polyaryl sulfones), atactic polystyrene, syndiotactic polystyrene ("sPS") and its derivatives (such as syndiotactic poly-alpha-methyl styrene and syndiotactic polydichlorostyrene), blends of any of these polystyrenes (with each other or with other polymers, such as polyphenylene oxides), copolymers of any of these polystyrenes (such as styrene-butadiene copolymers, styrene-acrylonitrile copolymers, and acrylonitrile-butadiene-styrene terpolymers), polyacrylates (such as polymethyl acrylate, polyethyl acrylate, and polybutyl acrylate), polymethacrylates (such as polymethyl methacrylate, polyethyl methacrylate, polypropyl methacrylate, and polyisobutyl methacrylate), cellulose derivatives (such as ethyl cellulose, cellulose acetate, cellulose propionate, cellulose acetate butyrate, and cellulose nitrate), polyalkylene polymers (such as polyethylene, polypropylene, polybutylene, polyisobutylene, and poly(4-methyl)pentene), fluorinated polymers and copolymers (such as polytetrafluoroethylene, polytrifluoroethylene, polyvinylidene fluoride, polyvinyl fluoride, fluorinated ethylene-propylene copolymers, perfluoroalkoxy resins, polychlorotrifluoroethylene, polyethylene-co-trifluoroethylene, polyethylene-co-chlorotrifluoroethylene), chlorinated polymers (such as polyvinylidene chloride and polyvinyl chloride), polyacrylonitrile, polyvinylacetate, polyethers (such as polyoxymethylene and polyethylene oxide), ionomeric resins, elastomers (such as polybutadiene, polyisoprene, and neoprene), silicone resins, epoxy resins, and polyurethanes.

Also suitable are copolymers, such as the copolymers of PEN discussed above as well as any other non- naphthalene group -containing copolyesters which may be formulated from the above lists of suitable polyester comonomers for PEN. In some applications, especially when PET serves as the first polymer, copolyesters based on PET and comonomers from the lists above (coPETs) are especially suitable. In addition, either first or second polymers may consist of miscible or immiscible blends of two or more of the above-described polymers or copolymers (such as blends of sPS and atactic polystyrene, or of PEN and sPS). The coPENs and coPETs described may be synthesized directly, or may be formulated as a blend of pellets where at least one component is a polymer based on naphthalene dicarboxylic acid or terephthalic acid and other components are polycarbonates or other polyesters, such as a PET, a PEN, a coPET, or a co-PEN.

Another preferred family of materials for the second polymer for some applications are the syndiotactic vinyl aromatic polymers, such as syndiotactic polystyrene. Syndiotactic vinyl aromatic polymers useful in the current invention include poly(styrene), poly(alkyl styrene)s, poly(aryl styrene)s, poly(styrene halide)s, poly(alkoxy styrene)s, poly(vinyl ester benzoate), poly(vinyl naphthalene), poly(vinylstyrene), and poly(acenaphthalene), as well as the hydrogenated polymers and mixtures or copolymers containing these structural units. Examples of poly(alkyl styrene)s include the isomers of the following: poly(methyl styrene), poly(ethyl styrene), poly(propyl styrene), and poly(butyl styrene). Examples of poly(aryl styrene)s include the isomers of poly(phenyl styrene). As for the poly(styrene halide)s, examples include the isomers of the following: poly(chlorostyrene), poly(bromostyrene), and poly(fluorostyrene). Examples of poly(alkoxy styrene)s include the isomers of the following: poly(methoxy styrene) and poly(ethoxy styrene). Among these examples, particularly preferable styrene group polymers, are: polystyrene, poly(p-methyl styrene), poly(m-methyl styrene), poly(p-tertiary butyl styrene), poly(p-chlorostyrene), poly(m-chloro styrene), poly(p-fluoro styrene), and copolymers of styrene and p-methyl styrene.

Furthermore, comonomers may be used to make syndiotactic vinyl aromatic group copolymers. In addition to the monomers for the homopolymers listed above in defining the syndiotactic vinyl aromatic polymers group, suitable comonomers include olefin monomers (such as ethylene, propylene, butenes, pentenes, hexenes, octenes or decenes), diene monomers (such as butadiene and isoprene), and polar vinyl monomers (such as cyclic diene monomers, methyl methacrylate, maleic acid anhydride, or acrylonitrile).

The syndiotactic vinyl aromatic copolymers of the present invention may be block copolymers, random copolymers, or alternating copolymers.

The syndiotactic vinyl aromatic polymers and copolymers referred to in this invention generally have syndiotacticity of higher than 75% or more, as determined by carbon-13 nuclear magnetic resonance. Preferably, the degree of syndiotacticity is higher than 85% racemic diad, or higher than 30%, or more preferably, higher than 50%, racemic pentad.

In addition, although there are no particular restrictions regarding the molecular weight of these syndiotactic vinyl aromatic polymers and copolymers, preferably, the weight average molecular weight is greater than 10,000 and less than 1,000,000, and more preferably, greater than 50,000 and less than 800.000.

The syndiotactic vinyl aromatic polymers and copolymers may also be used in the form of polymer blends with, for instance, vinyl aromatic group polymers with atactic structures, vinyl aromatic group polymers with isotactic structures, and any other polymers that are miscible with the vinyl aromatic polymers. For example, polyphenylene ethers show good miscibility with many of the previous described vinyl aromatic group polymers.

Particularly preferred combinations of polymers for optical layers in the case of mirrors or colored films include PEN/PMMA, PET/PMMA, PEN/"ECDEL," PET/"ECDEL," PEN/sPS, PET/sPS, PEN/coPET, PEN/PETG, and PEN/ "THV," where "PMMA" refers to polymethyl methacrylate, "ECDEL" refers to a thermoplastic polyester or copolyester (believed to comprise cyclohexanedicarboxylate units, polytetramethylene ether glycol units, and cyclohexanedimethanol units) commercially available under the trade designation "ECDEL" from Eastman Chemical Co., "coPET" refers to a copolymer or blend based upon terephthalic acid (as described above), "PETG" refers to a copolymer of PET employing a second glycol (usually cyclohexanedimethanol), and "THV" is a fluoropolymer commercially available under the trade designation "THV" from the 3M Company.

For mirror films, a match of the refractive indices of the first polymer and second polymer in the direction normal to the film plane is preferred, because it provides for constant reflectance with respect to the angle of incident light (that is, there is no Brewster's angle). For example, at a specific wavelength, the in-plane refractive indices might be 1.76 for biaxially oriented PEN, while the film plane-normal refractive index might fall to 1.49. When PMMA is used as the second polymer in the multilayer construction, its refractive index at the same wavelength, in all three directions, might be 1.495. Another example is the PET/"ECDEL" system, in which the analogous indices might be 1.66 and 1.51 for PET, while the isotropic index of "ECDEL" might be 1.52. The crucial property is that the normal-to-plane index for one material must be closer to the in-plane indices of the other material than to its own in-plane indices.

It is sometimes preferred for the multilayer optical films of the current invention to consist of more than two distinguishable polymers. A third or subsequent polymer might be fruitfully employed as an adhesion-promoting layer between the first polymer and the second polymer within an optical stack, as an additional component in a stack for optical purposes, as a protective boundary layer between optical stacks, as a skin layer, as a functional coating, or for any other purpose. As such, the composition of a third or subsequent polymer, if any, is not limited. Preferred multicomponent constructions are described in application having U.S. Ser. No. 09/006,118, filed Jan. 13, 1998 now U.S. Pat. No. 6,207,260.

Detailed process considerations and additional layers are included in application having U.S. Ser. No. 09/006,288, filed Jan. 13, 1998 now abandoned.

Further, color shifting films useful in the present invention are described in application having U.S. Ser. No. 09/006,591, filed Jan. 13, 1998. These color shifting films are multilayer birefringent polymeric films having particular relationships between the refractive indices of successive layers for light polarized along mutually orthogonal in-plane axes (the x-axis and the y-axis) and along an axis perpendicular to the in-plane axes (the z-axis). In particular, the differences in refractive indices along the x-, y-, and z-axes ($\Delta x$, $\Delta y$, and $\Delta z$, respectively) are such that the absolute value of $\Delta z$ is less than about one half (in some embodiments one quarter, or even one tenth) the larger of the absolute value of $\Delta x$ and the absolute value of $\Delta y$ (e.g., ($|\Delta z|$<0.1 k (in some embodiments 0.25 k, or even 0.1 k), k=max{$|\Delta x|$, $|\Delta y|$}). Films having this property can be made to exhibit transmission spectra in which the widths and intensities of the transmission or reflection peaks (when plotted as a function of frequency, or 1/1) for p-polarized light remain essentially constant over a wide range of viewing angles, but shift in wavelength as a function of angle. Also for p-polarized light, the spectral features shift toward the blue region of the spectrum at a higher rate with angle change than the spectral features of isotropic thin film stacks. In some embodiments, these color shifting films have at least one optical stack in which the optical thicknesses of the individual layers change monotonically in one direction (e.g., increasing or decreasing) over a first portion of the stack, and then change monotonically in a different direction or remain constant over at least a second portion of the stack. Color shifting films having stack designs of this type exhibit a sharp band edge at one or both sides of the reflection band(s), causing the film to exhibit sharp, eye-catching color changes as a function of viewing angle.

Glitter according to the present invention may be produced in any of a wide variety of desired sizes and shapes in any number of desired shapes (including copyrightable material or a trademark (e.g. movie or TV characters), including a registerable trademark or registered copyright as defined under the laws of the countries, territories, etc. of the world (including those of the United States)). The periphery of the glitter may be, for example, a regular, predetermined shape (e.g., circles, squares, rectangles, diamonds, stars, alphanumerics, symbols, other polygons (e.g., hexagons)), or an irregular random shape. The size and shape of the glitter is typically chosen to optimize the appearance of the glitter or to suit a particular end use application.

Glitter according to the present invention typically, and preferably, are produced by converting the film material into particles. Suitable conversion techniques are known in the art. Conversion services are also commercially available, for example, from Glitterex Corporation, Belleville, N.J. Conversion of the film into regular, predetermined shapes may be done, for example, using precision cutting techniques (e.g., rotary die cutting).

Multi-layer films suitable for use in making glitter of the present invention preferably have sufficient inter-layer adhesion to prevent delamination during the conversion process. The thickness of the film (in the z direction) from which glitter according to the present invention is preferably about 3 to about 25% of the smallest glitter particle dimension (i.e., measured in the respective x and y directions). Preferably, the glitter is sufficiently thick to remain flat in application, but not so thick as to create substantial edge effects (i.e., distortions on cut edges of the glitter particles that extend into a substantial portion of the film thickness).

Optionally, glitter according to the present invention can include coatings such as abrasion-resistant or hard coatings, anti-static coatings, ultra-violet light absorbing coatings, tinted coatings, adhesive materials, and/or the like to improve or provide certain properties. Although such materials can be applied to individual glitter particles, they are frequently most easily applied to a sheet of film material which is in turn converted into glitter.

Suitable abrasion resistant coatings, and techniques for applying the same, are known in art. Such materials include acrylic hardcoats (available, for example, under the trade designations such as "ACRYLOID A-11" and "PARALOID K-120N" from Rohm & Haas, Philadelphia, Pa.); urethane acrylates (including those described in U.S. Pat. No. 4,249, 011 (Wendling); as well as those available from Sartomer Corp., Westchester, Pa.); and polyurethane hardcoats obtained from the reaction of an aliphatic polyisocyanate (available, for example, under the trade designation "DES-MODUR N-3300" from Miles, Inc., Pittsburgh, Pa.) with a polyester polyol (available, for example, under the trade designation "TONE POLYOL 0305" from Union Carbide, Houston, Tex.

Suitable antistatic coatings or films, and techniques for applying the same, are known in art. Such materials, which may improve the processability of the film for the particulating process, and or the flowabilty of the individual particles, include $V_2O_5$ and salts of sulfonic acid polymers, carbon (including carbon black), and metals. A preferred vanadium oxide antistatic coating is described in U.S. Pat. No. 5,407,603 (Morrison).

Suitable ultra-violet (UV) light absorbing coatings or films, and techniques for applying the same, are known in art. Such materials, which may provide protection from UV radiation, include UV stabilized films and coatings such as those which incorporate benzotriazoles (available, for example, from Ciba Geigy Corp., Hawthorne, N.Y.) or hindered amine light stabilizers (HALS) (available, for example, under the trade designation "TINUVIN 292", from Ciba Geigy Corp.), and those which contain benzophenones or diphenyl acrylates (available, for example, from BASF Corp., Parsippany, N.J.). Ultra-violet (UV) light absorbing coatings or films may be particularly useful in applications where the glitter particles are exposed to a significant amount of light in the UV region of the spectrum (e.g., when used outdoors in the day light).

Examples of adhesive materials, which can be applied using techniques known in the art, include pressure sensitive adhesives, hot-melt adhesives, solvent-coated adhesives, heat activated adhesives and the like. These adhesive materials preferably are optically clear, diffuse and exhibit non-hazy and non-whitening aging characteristics. Furthermore, the adhesive materials should exhibit long term stability under high heat and humidity conditions. Suitable adhesive materials may include solvent, heat, or radiation activated adhesive systems. Pressure sensitive adhesive materials are normally tacky at room temperature and can be adhered to a surface by application of light to moderate pressure.

Examples of adhesive materials, whether pressure sensitive or not and useful in the present invention include those based on general compositions of polyacrylate; polyvinyl ether; diene-containing rubbers such as natural rubber, polyisoprene, and polyisobutylene; polychloroprene; butyl rubber; butadieneacrylonitrile polymers; thermoplastic elastomers; block copolymers such as styrene-isoprene and styrene-isoprene-styrene block copolymers, ethylenepropylene-diene polymers, and styrene-butadiene polymers; polyalphaolefins; amorphous polyolefins; silicone; ethylene-containing copolymers such as ethylene vinyl acetate, ethylacrylate, and ethylmethacrylate; polyurethanes; polyamides; polyesters; epoxies; polyvinylpyrrolidone and vinylpyrrolidone copolymers; and mixtures of the above.

Additionally, adhesive materials can contain additives such as tackifiers, plasticizers, fillers, antioxidants, stabilizers, diffusing particles, curatives, and solvents, provided they do not interfere with the optical characteristics of the devices. When additives are used they are used in quantities that are consistent with there intended use and when used to laminate an optical film to another surface, the adhesive composition and thickness are preferably selected so as not to interfere with the optical properties of the optical film.

Further, the surface(s) on which an adhesive material is applied or otherwise attached to may be primed (e.g., chemically, physical (e.g., physical treatment such as roughening), and corona) to affect the degree of attachment between the adhesive material and surface.

The visual appearance of the glitter (e.g., visible mirror film glitter) may be affected by the background on which it is viewed. For example, the visual appearance of the visible mirror film glitter is typically different for a black background than for, for example, a white background. Thus, for some applications, it may be desirable for the adhesive material to include additives such as carbon black particles (which tend to make the adhesive material black) or $TiO_2$ particles (which tend to make the adhesive material white) to affect the color and/or translucency of the adhesive material In addition, or alternatively, an ink (e.g., a black or white ink) layer or the like may be placed on the visible mirror film and/or the background on which the glitter is placed or viewed may be selected to provide a desired effect on visual appearance of the visible mirror film.

Another background, which may be preferred in some applications is a mirrored background (e.g., by use of a visible mirror film, as well as with other mirrored materials).

Examples of polymeric matrix materials include thermoplastics (high density polyethylene, low density polyethylene, polypropylene, ethylene/vinyl acetate, polystyrene, polymethylpentene, acrylonitrile-butadiene-styrene (ABS), poly(vinyl butyral), poly(vinyl chloride), polytetrafluoroethylene, poly(vinyl fluoride), polyamides (e.g., nylon), poly(methyl methacrylate), urethanes, polycarbonate, poly(ethylene terephthalate), poly(butylene terephthalate); thermosets (phenolics, amino resins, epoxies, unsaturated polyesters, and crosslinked polyurethanes); and elastomers (natural and synthetic rubber (including vulcanized rubber)), polyacrylates, polyester and polyether urethanes, polybutadiene, silicone elastomers, isobutene-isoprene copolymer (butyl), and acrylonitrile-butadiene copolymer (nitrile). Additional examples of matrix materials, some of which may also be polymeric materials, include adhesive materials, such as natural rubber based pressure sensitive adhesives, acrylic pressure sensitive adhesives, hot melt adhesives. Matrix materials may further comprise optional additives (e.g., antimicrobials, antistats, blowing agents, colorants (e.g., to tint, or otherwise impart or alter the color of, the matrix material), curatives, fillers, dispersion aids, thickeners, thinners, flame retardants, impact modifiers, initiators, lubricants, plasticisers, slip agents, and stabilizers) which provide, for example, a desirable feature or property in the final composite article comprising the glitter, and/or add in the processing step(s) to make the article.

Techniques for incorporating glitter according to the present invention into the matrix material include those known in the art for incorporating conventional glitters into matrix materials. For example, glitter can be dispersed in a liquid, for example, by mixing or otherwise agitating the liquid with glitter therein. Dispersion of the glitter in the liquid may be aided, for example, with the use of dispersion aids. In some cases, a liquid having glitter dispersed therein is a precursor for a composite article derived therefrom. For example, glitter can be dispersed in a curable polymeric material wherein the glitter containing polymeric material is placed in a mold having the shape of the desired final article, followed by the curing of the polymeric material.

Articles comprising glitter-containing matrix materials may be made by any of a variety of techniques including cast molding, injection molding (particularly useful, for example, to make three-dimensional articles); extrusion (particularly useful, for example, to make films, sheet materials, fibers and filaments, cylindrical tubes, and cylindrical shells (i.e., pipe). Sheet or film materials may comprise a single layer or a plurality of layers (i.e., a multiple-layered construction). Multiple layer constructions may have the glitter in one or more of the layers, and may optionally contain different shapes, sizes, and concentrations of glitter in different layers.

Further, for example, glitter according to the present invention may be incorporated into, or mixed with, polymer pellets suitable for injection molding. Other examples of processes for incorporating glitter according to the present invention into a matrix material of a finished article include vacuum molding, blow molding, rotomolding, thermoforming, extruding, compression molding, and calendering.

The orientation of the glitter in the matrix material may, for example, be random with respect to one another, or have substantially the same orientation relative to one another or relative to a surface of the matrix material. Alignment or orientation of the glitter within the matrix material may be provided, for example, by high shear processing (e.g., extrusion or injection molding) of glitter-containing matrix material which results in orientation or alignment of the glitter along the flow direction of the matrix material. Other techniques for orientating the glitter within a matrix material may be apparent to those skilled in the art after reviewing the disclosure of the present invention.

Turning again to liquids having glitter according to the present invention therein, such dispersions, or dispersible combinations may be solvent-borne (i.e., dissolved in an organic solvent), water-borne (i.e., dissolved or dispersed in water), single component, or multi-component. When the dispersions, or dispersible combinations are to be used to provide a coating on a surface, the liquid may preferably be a film-forming material.

Examples of liquid mediums, although the compatibility (e.g., chemical compatibility), and hence the suitability of a particular liquid will depend, for example, on the composition of the glitter, as well as other components of the dispersions, or dispersible combinations, include water, organic liquids (e.g., alcohols, ketones (for a short period of time)), and mixtures thereof. It is noted that some matrix materials may sometimes be liquids, and other times a solid. For example, at room temperature, typical hot melt adhesive materials are solids, whereas when heated to their respective melting points, they are liquids. Further, for example, a liquid glue, prior to curing and/or drying is a liquid, but after curing and/or drying, is a solid.

The dispersions, or dispersible combinations, may be, for example, dryable, curable, or the like to form yet another matrix (e.g., a paint may be dried or cured to provided a solid or hardened form). The dispersions, or dispersible combinations, may include additives (e.g., antimicrobials, antistats, blowing agents, colorants or pigments (e.g., to tint, or otherwise impart or alter the color of, the matrix material), curatives, thinners, fillers, flame retardants, impact modifiers, initiators, lubricants, plasticisers, slip agents, stabilizers, and coalescing aids, thickening aids, dispersion aids, defoamers, and biocides) which provide, for example, a desirable feature or property in the desired final composite (comprising the glitter), and/or aid in the processing step(s) to make the desired final composite (comprising the glitter).

In one aspect, the dispersion, or dispersible combination includes binder precursor material (i.e., a material that is convertable from a liquid (i.e., a flowable form) e.g., polymers dissolved in a solvent, polymer precursors dissolved in a solvent, polymer emulsions, and curable liquids) into a solidified or hardened form. Processes to convert a liquid binder precursor material to a solidified or hardened binder material include evaporation of a solvent, curing (i.e., hardening via chemical reaction), and combinations thereof.

Additional examples of binder precursors and binders for the dispersions, or dispersible combinations, containing glitter according to the present invention include vinyl polymers, vinyl-acrylic polymers, acrylic polymers, vinyl-chloride acrylic polymers, styrene/butadiene copolymers, styrene/acrylate copolymers, vinyl acetate/ethylene copolymers, animoalkyl resin, thermosetting acrylic resins, nitrocellulose resins, modified acrylic lacquer, straight chain acrylic lacquer, polyurethane resin, acrylic enamel resin, silyl group-containing vinyl resin, and combinations thereof.

Examples of dispersions or dispersible combinations, that can contain glitter according to the present invention include fingernail polish, paint (including paint for automotive and marine applications, indoor and outdoor house paint, art and crafts paint, hobby paints (e.g., toy model paints), and finger paints). Such dispersions or dispersible combinations, are typically applied to a surface to provide a coating which is subsequently dried, cured, or the like to provide a hardened or non-wet surface coating.

A particularly preferred embodiment of the present invention is cosmetic compositions comprising glitter according to the present invention. Thus, glitter may be incorporated into powders, lotions, semi-solid stick, liquids, creams and gels suitable for application to the face, body and/or hair of people or animals. More specifically, glitter of the present invention may be advantageously incorporated in hair styling compositions, face adornment composition and body adornment compositions. Such compositions may be applied to the body by pump spraying or arosol spraying, painting on using a brush, sponge, cloth or the like, or applicator such as a wooden or plastic stick, swab, or the finger.

Specific examples of cosmetic formulations include hair spray, hair gel, hair mousse, lipstick, lipgloss, face powder, liquid cosmetic foundation, body paint, body powder, fingernail polish, eyeshadow, eyeliner, concealer stick, blush stick, mascara, cosmetics that may be applied to the teeth, moustache wax, rouge, massage oil and the like.

The glitter of the present invention may be formulated with other cosmetics with such cosmetic ingredients as the formulator may find useful such as (but not limited to); hydrocarbon waxes, solvents polymers (linear, graft, elastomeric, co-) and gels; silicon containing polymers, waxes solvents and gels; film-forming polymers, phase separating polymers, microphase separating polymers, film forming agents (such as trisiloxysilicate), gelling agents (such as clay or artificial clay), fluorocarbon solvents and polymers, and the like.

Additionally, compositions of the present invention may further comprise medicaments or other active ingredients in the composition. For example, the composition may comprise anti-itching medicaments or topical pain relief medicaments. Alternatively, the composition may incorporate UV absorbing components, to provide a glitter-containing sunscreen. Compositions containing such active ingredients may benefit from incorporation of glitter by identifying to the user all places where such composition has been applied, thereby ensuring complete coverage of the intended substrate area by the composition, and ensuring that the composition is not over-applied to areas that have already been covered.

Cosmetic compositions according to the present invention provide particular benefit in supplying excellent visual appearance properties.

The size, shape, thickness, and amount of glitter used in a particular application, including applications described herein, may depend on a number of factors, including the desired effect to be achieved, cost, inherent limitations of the application (e.g., if the glitter is in a binder material, the amount of glitter should not exceed the loading capacity of the binder matrix, unless it is desired for excess glitter to easily fall out), and for liquid matrices, the viscosity of the dispersions, or other physical properties or performance characteristics of a matrix having the glitter therein.

Glitter according to the present invention may also be applied to a surface by first applying a binder or adhesive material, then applying the glitter, followed by drying, curing, solidification, or the like of the binder or adhesive material.

Examples of substrate for adhering the glitter to include toys, fabrics, sheet materials (e.g., paper, cardboard, and films), ornaments, plastics, wood, and metal. Adhering glitter to the surface of a substrate can. for example, provide a decorative effect.

The glitter may be adhered to the surface using any suitable form of attachment, such as glue, pressure sensitive adhesive, hot-melt adhesive, and stitching. When adhered with adhesive materials, the glitter can, for example, be placed onto, or broadcasted over, the surface of the adhesive-coated substrate. Placement of the glitter relative to the substrate may be provided in any of a variety of desired patterns and/or orientations.

For example, the glitter can be randomly or uniformly over the surface, and can be random in some areas of the surface and uniform in others. Further, for example, the glitter can be randomly or uniformly (e.g.. uniformly spaced) oriented with respect to the surface, and can be randomly oriented in some areas and uniformly oriented in others. The glitter can be patterned to provide, or be a part of, copyrightable material or a trademark (e.g. movie or TV characters), including a registered or registrable trademark under any of the laws of the countries, territories, etc. of the world. Optionally, a coating (e.g., a clear coating) may be applied over at least a portion of the glitter to provide additional bonding to the substrate, to provide protection to the glitter, or to provide a more visually appealing effect.

Figure 5:
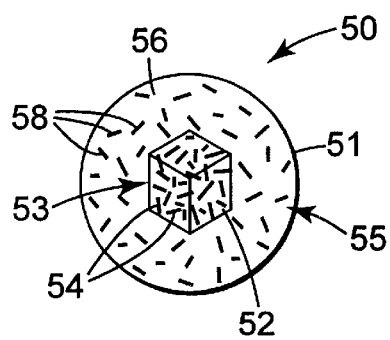
Figure 6:
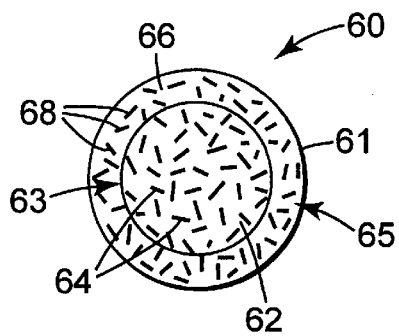
Figure 7:
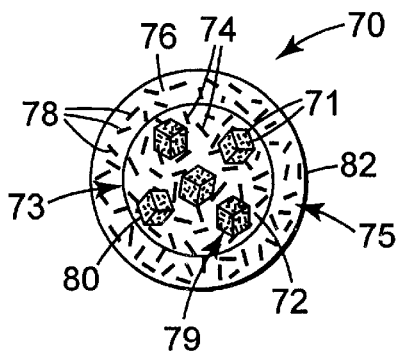
Figure 8:
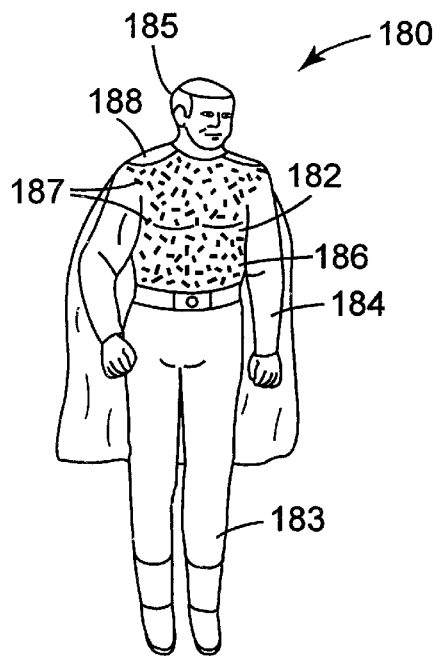
FIG. 8 is a perspective view of an action figure according to the present invention.
Figure 9:
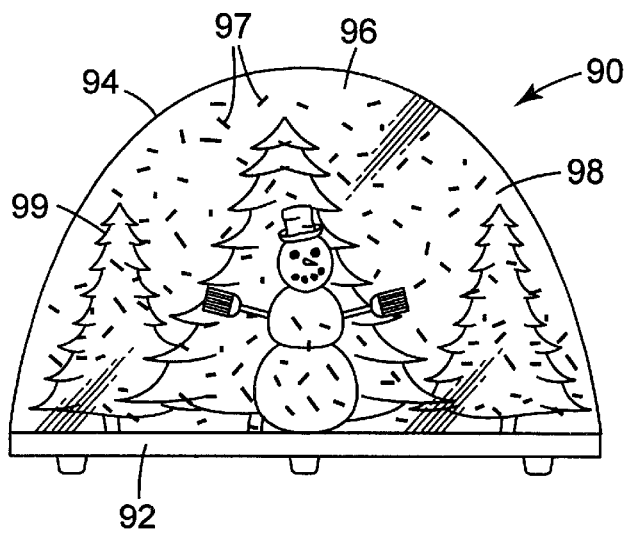
FIG. 9 is a perspective view of a winter scene globe according to the present invention.

To further illustrate examples of matrices having glitter according to the present invention dispersed therein, several exemplary articles are shown in FIGS. 1–10 and 14–18, which include in FIGS. 6, 7, and 9, examples of glitter dispersed a liquid (e.g., water). Further, FIGS. 11–13 (and 14–18), articles having glitter attached to thereto.

Referring to FIG. 1, toy ball 10 has substantially spherical major surface 11, matrix material 12 (e.g., a material such as a silicone, rubber, urethane, or polyvinyl chloride (PVC)), and glitter according to the present invention 14 randomly dispersed therein. Matrix material 12 (as shown) is sufficiently translucent (optionally clear) such that an object can be viewed by looking through the ball. Alternatively, for example, the matrix material is opaque (e.g., black) such that only glitter at the periphery of the ball is viewable. Ball 10 can be made, for example, by injection molding a glitter-containing liquid, polymeric material, curing the polymeric material, and then removing the resulting ball from the mold.

Figure 2:
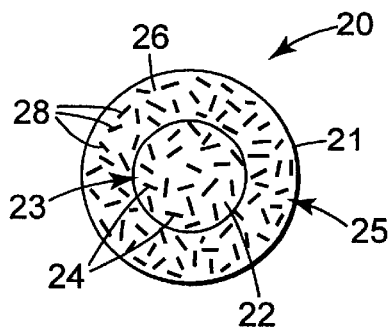

Referring to FIG. 2, toy ball 20 has substantially spherical major surface 21, inner, spherical region 23, and outer, spherical region 25. Inner region 23 comprises first matrix material 22 and first glitter 24 dispersed therein, and outer region 25 comprises second matrix material 26 and second glitter 28 dispersed therein, wherein at least one of glitter 24 or 28 is glitter according to the present invention. Optionally, matrix material 22 is different from matrix material 26. In one embodiment, for example, both first matrix material 22 and second matrix material 26 are each translucent, but the degree of translucency of matrix material 22 is greater than that of matrix material 26. In another embodiment, for example, matrix material 22, which may optional have glitter 24 herein, is opaque (e.g., black), and outer region 25 is translucent such that the color or visual effect of inner region 23 is viewable from the periphery of the ball. Ball 20 can be made, for example, by injection molding a glitter-containing liquid, polymeric material, curing the polymeric material, and then removing the resulting ball from the mold to provide inner region 23; outer region 25 can be formed by injection molding to provide two half sphere pieces which are in turn placed over the inner region and the two outer pieces secured together (e.g., using a liquid adhesive material).

Figure 3:
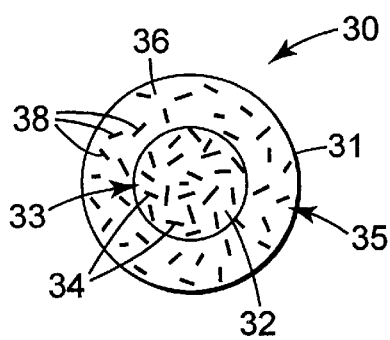

Referring to FIG. 3, toy ball 30 has substantially spherical major surface 31, inner region 33, and outer region 35. Inner region 33 comprises first matrix material 32 and first glitter 34 dispersed therein, and outer region 35 comprises second matrix material 36 and second glitter 38 dispersed therein, wherein at least one of glitter 34 or 38 is glitter according to the present invention, and wherein the average concentration of glitter (i.e., volume of glitter per unit volume) in inner region 33 is greater than that in outer region 35. Optionally, matrix material 32 is different from matrix material 36. In one embodiment, for example, both first matrix material 32 and second matrix material 36 are each translucent, but the degree of translucency of matrix material 36 is greater than that of matrix material 32.

Figure 4:
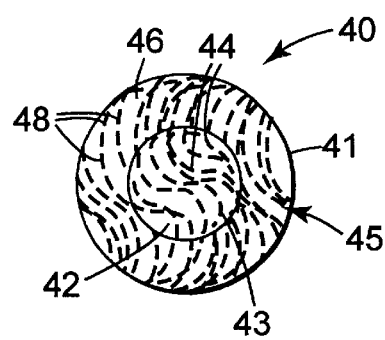

Referring to FIG. 4, toy ball 40 has substantially spherical major surface 41, inner region 43, and outer region 45. Inner region 43 comprises first matrix material 42 and first glitter 44 dispersed therein, and outer region 45 comprises second matrix material 46 and second glitter 48 dispersed therein, wherein at least one of glitter 44 or 48 is glitter according to the present invention, and wherein each glitter particle has a width and length that are substantially greater than the thickness of a respective particle, and. wherein at least one of glitter 44 or 48 are generally oriented in shown in the swirl patterns in FIG. 4. Optionally, matrix material 42 is different from matrix material 46. In one embodiment, for example, both first matrix material 42 and second matrix material 46 are each translucent, but the degree of translucency of matrix material 46 is greater than that of matrix material 42. In another embodiment, for example, matrix material 42, which may optional have glitter 44 herein, is opaque (e.g., black), and outer region 45 is translucent such that the color or visual effect of inner region 43 is viewable from the periphery of the ball.

Referring to FIG. 5, toy ball 50 has substantially spherical major surface 51, non-spherical, inner region 53, and outer, spherical region 55. Inner region 53 comprises first matrix material 52 and first glitter 54 dispersed therein, and outer region comprises second matrix material 56 and second glitter 58 dispersed therein, wherein at least one of glitter 54 or 58 is glitter according to the present invention. Optionally, matrix material 52 is different from matrix material 56. In one embodiment, for example, both first matrix material 52 and second matrix material 56 are each translucent, but the degree of translucency of matrix material 56 is greater than that of matrix material 52. In another embodiment, for example, matrix material 52, which may optional have glitter 54 herein, is opaque (e.g., black), and outer region 55 is translucent such that the color or visual effect of inner region 53 is viewable from the periphery of the ball. Non-spherical region 53 can be in any number of desired shapes (e.g., copyrightable material or a trademark (e.g. movie or TV characters)).

Referring to FIG. 6, toy ball 60 has substantially spherical major surface 61, inner region 63, and outer, spherical region 65. Inner region 63 comprises liquid or gel 62 and first glitter 64 dispersed, or dispersible, therein, and outer region comprises matrix material 66 and optional second glitter 68 dispersed therein, wherein at least one of glitter 64 or 68 is glitter according to the present invention. Optionally, liquid or gel 62 is tinted, rather than merely clear.

Referring to FIG. 7, toy ball 70 has substantially spherical major surface 71, inner region 73, and outer, spherical region 75. Inner region 73 comprises liquid or gel 72, pieces 79, and first glitter 74 dispersed. or dispersible, therein, and outer region comprises first matrix material 76 and second glitter 78 dispersed therein Pieces 79 are shown comprising second matrix material 80 and second glitter 82 dispersed therein Only one of glitter 74, 78, and 82, need be present, and at least one of the glitters present is glitter according to the present invention. Optionally, liquid or gel 72 is tinted, rather than merely clear.

The general concepts illustrated in FIGS. 1–7, which are not meant to be exhaustive, with regard, for example, to types of matrices, combinations of matrices, glitter, and combinations of glitter in constructions, are adaptable to any of a wide variety of other articles as well. To illustrate this point, a few such examples are shown in FIGS. 8–18.

Referring to FIG. 8, doll or action figure 180 comprises torso 182, legs 183, arms 184, and head 185. Torso 182 comprises first matrix material 186 and second matrix material 188. First matrix material 186, which has glitter according to the present invention 187 dispersed therein, is sufficiently translucent to allow second matrix material 188, which is preferably more darkly colored (e.g., black) than first matrix material 186, to be observed there through.

Doll or action figure 180 can be made, for example, using conventional processing techniques in which glitter according to the present invention is utilized as a raw material. For example, first matrix material 186 could first be made in sheet form having glitter according to the present invention dispersed therein. Such sheet could then be formed into the desired final shape, for example, by vacuum form techniques. The form sheet could them be placed in a mold (for the doll or action figure), and the mold filled with a precursor of second matrix material 188. Such precursor material could then be converted to provide doll or action figure 180.

Referring to FIG. 9, winter scene globe 90 comprises transparent dome 94, which is attached to base 92 to provide sealed chamber 96. Sealed chamber 96 contains liquid 98 (e.g., water), winter or holiday scene 99, and a plurality of glitter according to the present invention 97. Glitter 97 can be dispersed in liquid 98 by shaking globe 90. After shaking, the glitter will settle through liquid 98, due to gravity, simulating a "snowfall." Typically liquid 98 is clear, although other liquids can also be used, and the liquid can optionally be tinted.

Figure 10:
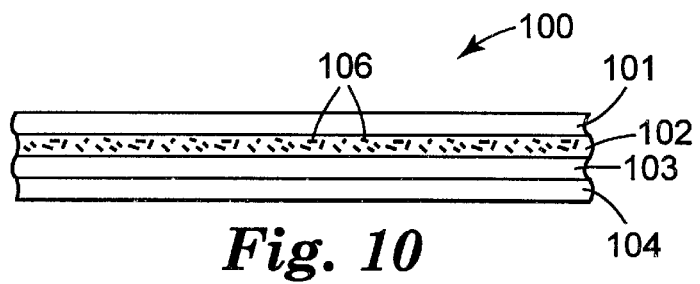
FIG. 10 is a side view in cross-section of a multi-layered film according to the present invention.

Referring to FIG. 10, sheet material (e.g., multi-layer film (e.g., polymeric film made, for example, of polyethylene, polypropylene. or polyester)) 100 comprises a plurality of layers, four of which are shown as 101, 102, 103, and 104. At least one layer includes glitter according to the present invention dispersed therein. For example, as shown 102 has glitter 106 randomly dispersed therein. Typically a sufficient number of layers are translucent in order to allow light incident upon the film to reach glitter 106 For example, glitter 106 is to be viewed through layer 101, such layer must be sufficiently translucent to enable a viewer to see through it to view glitter 106. Further, if the viewer is to see glitter embedded in layer 102, such need would also need to be sufficiently translucent to allow the viewer to see glitter 106. Optionally, one or more film layers may be tinted or colored to provide a contrasting background for the glitter. As shown in FIG. 10, the glitter may be present in multiple layers and individual glitter particles may overlap other particles depending upon the concentration of glitter particles in the film. The glitter may be oriented in a random fashion relative to one another or may have a non-random orientation. The orientation of the glitter may depend, for example, upon the size and shape of the glitter, the method of manufacturing of the film, and the concentration of glitter in the film. For example, during the process of extruding a polymeric film containing glitter, the extruded polymer is typically oriented (i.e., stretched) in the machine direction and/or in the cross-web direction. The orienting process may result in the glitter particles aligning with a major surface of the polymeric film (i.e, the major surface of the glitter is coplanar with a major surface of the polymer film).

Figure 11:
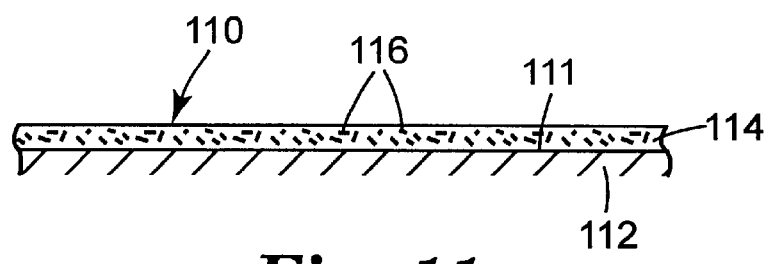
FIG. 11 is a side view in cross section of a coating according to the present invention adhered to a substrate.

Referring to FIG. 11, glitter-containing coating 110 is present on surface 111 of substrate 112. Coating 110 comprises translucent binder material 114 having glitter 116 randomly dispersed therein. Substrate 112 may be any of a variety of substrates, including a decorative ornament (such as that put on a tree; such ornament optionally includes a motor mechanism that allows the ornament to spin whereby a desirable visual effect can be obtained by when light interacts with the glitter), a plastic or paper sheet, jewelry, and fabric.

Figure 12:
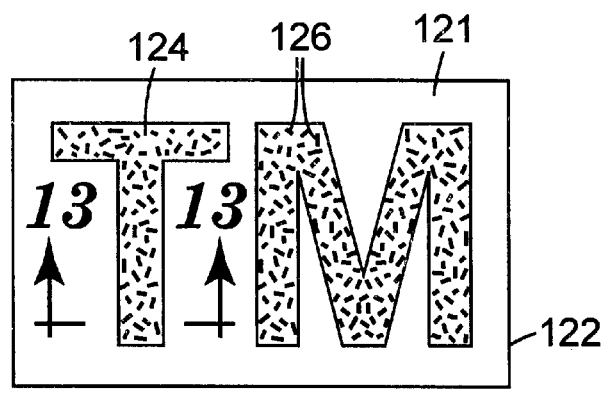
FIG. 12 is a top view of glitter according to the present invention adhered to a surface.
Figure 13:
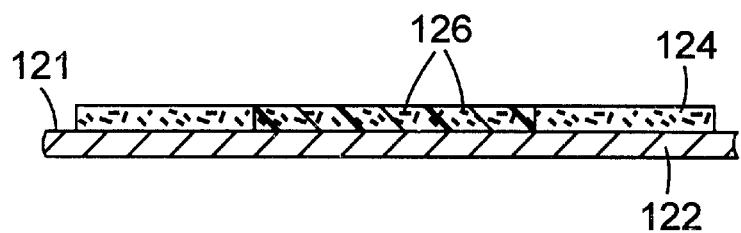
FIG. 13 is a side view in cross section of glitter according to the present invention adhered to a surface as illustrated in FIG. 12.

Referring to FIGS. 12 and 13, glitter 126 is shown adhered to binder material (e.g., an adhesive material such as a hot melt adhesive or a pressure sensitive adhesive 124, which in turn is adhered to surface 121 of substrate 122. As shown glitter 126 is in a pattern form. Optionally, for example, glitter 126 can be uniformly distributed or even in an oriented direction (e.g., arranged so that the thickness of the particles are perpendicular to, or parallel to surface 121. Substrate 122 may be any of a variety of substrates, including a decorative ornament (such as that put on a tree; such ornament optionally includes a motor mechanism that allows the ornament to spin whereby a desirable visual effect can be obtained by when light interacts with the glitter), a plastic or paper sheet, jewelry, and fabric.

In another aspect, glitter according to the present invention can be utilized to provide a hand-holdable toy light tube comprising a handle (including a first end), a tube (including a cylinder or cone) (e.g., a tube of film) extending from the first end, and a light source (i.e., the article includes a source that generates light as opposed to one that merely reflects ambient light) connected (including within) to the handle, wherein the light source is configured to be activated by a power source. The glitter according to the present invention can be incorporated into any of a number of locations on and/or within the hand holdable light tube. For example, the glitter can be disposed within the tube (e.g., in loose form inside the tube and/or in the material making up the tube or present) and/or on a major surface (e.g., the interior and/or exterior surface) of the tube. Preferably the light source is disposed at the first end of the handle. In another aspect, the light source is preferably a point light source (e.g., a flashlight). When energized or activated, the light source interacts with at least a portion of the tube glitter, producing an optical effect (typically a brilliant, multi-colored effect) visible to the user and/or observer(s). Optionally, the toy light tube includes a power source electrically coupled to the light source in conjunction with a switch to control activation to the light source.

While the light source is described as being connected to the handle, it is understood that the light source can be connected directly to the handle, or alternatively, connected to the handle via an intermediate structure or element.

Figure 14:
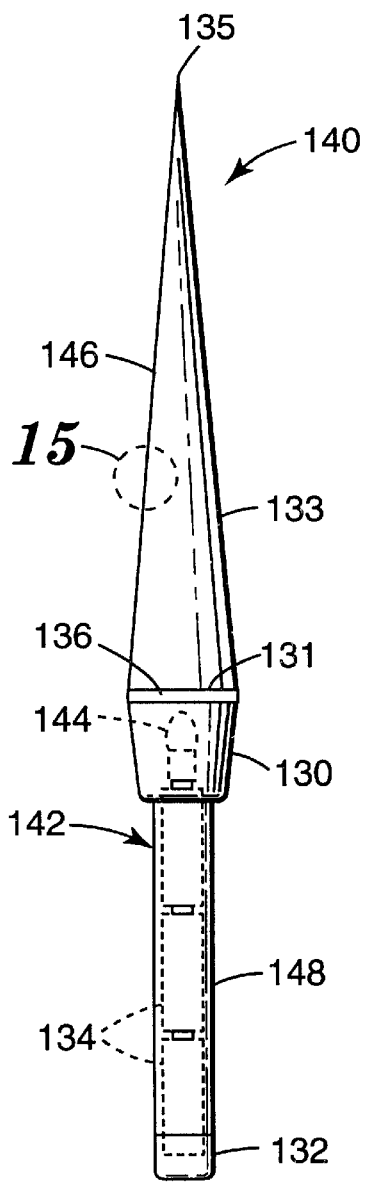
FIG. 14 is a side view of a hand-holdable toy light tube according to the present invention.
Figure 15:
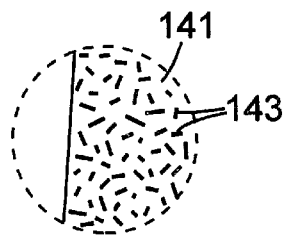
FIG. 15 is a cutaway view of a portion of the of the hand-holdable toy light tube of FIG. 14.

Referring to FIGS. 14 and 15, hand-holdable (e.g., a toy) light tube 140 includes handle 142, light source (e.g., a flashlight) 144, tube 146, and glitter according to the present invention (e.g., glitter 143 in translucent matrix material 141). Handle 142 has body 148 and ends 130, 132. Light source 144 is connected to the handle and is configured to be powered by power source 134 (e.g., batteries shown in dashed lines), and is disposed at end 130 of handle 142. Tube 146 extends from end 130 of handle 142. The glitter can be incorporated into any of a number locations on and/or within hand-holdable light tube 140. For example, the glitter can be disposed within matrix material 141 as shown in FIG. 15, attached to the major interior and/or major exterior surface of tube 146, and/or present in loose form within tube 146.

Tube 146 can be disposed in a number of different manners. Activation of point light source 144 directs light within at least a portion of tube 146. Tube 146, which is partially translucent (or transmissive) transmits, light from light source 144.

In one preferred embodiment, hand-holdable toy light tube 140 resembles an elongated cone or sword, although the tube can also be, for example, cylindrical tube or a conical section. Body 148 is preferably hollow to contain power source 134 (e.g., a battery) for powering light source 144. End 132 is preferably threadably secured to body 148, and end 130 is preferably rotatably secured to body 148.

End 130 is preferably configured to receive and maintain light source 144. Further, end 130 optionally includes translucent or filtered leading edge 136 (e.g., a clear lens) through which light from light source 144 can pass. In this regard, end 130 is configured to direct light from light source 144 to leading edge 136.

In one preferred embodiment, handle 142 is, or is similar to, a flashlight wherein, for example, body 148 and ends 130, 132 can be manufactured separately, but are configured for integral attachment. In this regard, end 132 can be threadably secured to body 148 to maintain power source 134 within body 148. End 130 is preferably rotatably secured to body 148 and acts as a switch operably connected between power source 134 and light source 144. That is, rotation of end 130 relative to body 148 moves light source 144 into and out of electrical contact with power source 134. Alternatively, for example, end 130 can be permanently secured to body 148 and finger-operated switch can be disposed, for example, along an outer circumference of body 148 for activating light source 144.

Components of hand-holdable toy light tubes can be made of any suitable material, including those disclosed herein. although some materials may be more suitable than others depending, for example, upon the particular toy use. For example, suitable materials for the handle may include rigid material (e.g., hard plastic, aluminum, stainless steel or wood) or more flexible materials such as rubber.

The light source can be, for example, electrical and/or chemical (e.g., chemiluminescent (see e.g., U.S. Pat. No. 4,717,511 (Koroscil), U.S. Pat. No. 5,043,851 (Kaplan), and U.S. Pat. No. 5,232,635 (Van Moer et al.))). Preferably, the light source emits visible (i.e., electromagnetic radiation having one or more wavelengths in the range from about $4 \times 10^{-7}$ m to $7 \times 10^{-7}$ m) and/or UV radiation (i.e., electromagnetic radiation having one or more wavelengths in the range from about $6 \times 10^{-8}$ m to $4 \times 10^{-7}$ m), although for some uses (e.g., photographic or electronic recording) other wavelengths of radiation compatible with the recording media or recording sensor may also be useful. Further, it is understood that one skilled in the art would select a light source for emitting the wavelength(s) of light and an optical film (e.g., a visible mirror film) to provide a desired visual effect.

The light source is preferably an incandescent light bulb, although other light sources such as a black light lamp, a halogen lamp, or a light emitting diode can also be used. The light source may include a plurality of lamps. Even further, for example, the light source can be configured to have a spikey spectral distribution. Preferably, the light source emits radiation toward the tube of sheet or film material. Preferred light sources which also have handles include flashlights (including those marketed by MAG Instrument of Ontario, Calif. under the trade designation "MAGLITE").

Referring again to FIG. 14, tube 146 is preferably formed into a cone having a first, proximal end 131, intermediate portion 133, and second, distal end 135. Proximal end 131 is configured for attachment to end 130 of handle 142. Intermediate portion 133 extends from proximal end 131 and is preferably constructed to be relatively rigid. Distal end 135 is unattached or free. Thus, tube 146 is configured such that movement of handle 142 imparts a similar movement onto tube 146. In other words, tube 146 will move in the same direction as handle 142.

As described in greater detail below, tube 146 can be formed by wrapping or curving a continuous sheet or film material. Further, because tube 146 is typically relatively rigid, the extended position of tube 146 relative to handle 142 is generally maintained regardless of the position or movement of handle 142.

Hand-holdable toy light tube 140 of one preferred embodiment can be constructed, for example, as follows. Light source 144 (e.g., a flashlight) is disposed at or near end 130 of handle 142. Tube 146 is curved or wrapped relative to handle 142 such that proximal end 131 is formed about and attached to end 130 of handle 142 by an adhesive material (e.g., adhesive tape, curable liquid adhesive, or the like). In one preferred embodiment, tube 146 is curved to form a cone, such that distal end 135 forms a closed tip. Thus, an interior of tube 146 is typically filled with air, although other mediums permitting passage of light may also be useful. In other embodiments according to the present invention. distal end 135 need not be closed. In other words, tube 146 may be curved relative to handle 142 such that distal end 135 is open, so that tube of sheet or film material 146 is a right cylinder. With this configuration, some light will pass outwardly from distal end 135, projecting onto a nearby wall or ceiling. It is also within the scope of the present invention to close distal end 135 (e.g., it can be covered with a film or sheet material, such as color shifting film). Even further, while tube 146 is shown as having a circular cross-section, other shapes are acceptable. For example, the tube may be elliptical in cross-section. Alternatively, for example, the tube may have a polyhedral cross-section, such as hexagonal or octagonal.

During use, light source 144 in one preferred embodiment is activated by rotating end 130 of handle 142 relative to body 148, although other ways of activating light source 144 (e.g., a separate switch) are also useful. In one preferred embodiment, light from light source 144 is directed through leading edge 136 of handle 142 into tube 146.

The visual appearance of tube 146 can be altered, for example, by including a translucent filter at a leading edge of the handle (e.g., leading end 136 of handle 142 in FIG. 14). The filter can alter the wavelengths of light emitted by the light source, thus varying the color(s) produced by the tube. For example, the filter can be configured to concentrate or diffuse the light emitted by the light source. Even further, the filter could be configured to concentrate the light in some areas and diffuse the light in others. Optionally, the filter is or includes a color shifting film.

Figure 16:
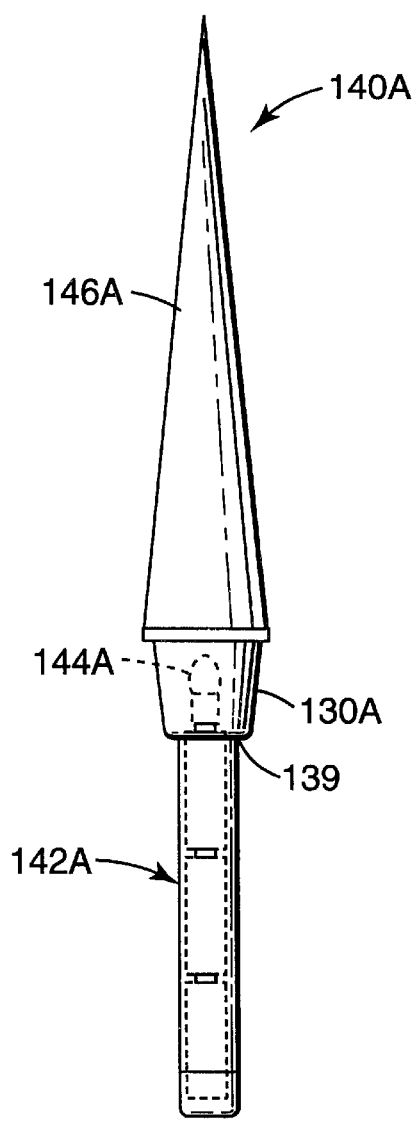
FIG. 16 is a side view of another hand-holdable toy light tube according to the present invention.

In some embodiments according to the present invention (see, e.g., FIG. 14) tube 146 is attached directly to an end of the handle. Other forms of attachment are also useful. For example, FIG. 16 illustrates an alternative embodiment of hand-holdable toy light tube according to the present invention 140A, which is similar to device 140 shown in FIG. 14. Toy light tube 140A includes handle 142A, light source 144A, tube 146A, and attachment body 139 for connecting tube 146A to end 130A of handle 142A. Although attachment body 139 is shown as a band of a color shifting film integrally formed with tube 146A, it may be in other suitable forms, such as opaque or translucent plastic, or a mirrored material (e.g., a visible mirror film). Attachment body 139 can be, for example, a disk or ring attached to end 130A of handle 142A. Tube 146A is attached to and extends from attachment body 139.

Another exemplary embodiment of a hand-holdable toy light tube according to the present invention is shown in FIG. 17. Hand-holdable toy light tube 160 includes handle 162, light source (not shown), attachment body 164, tube 166 (made of a translucent film or sheet material), glitter according to the present invention (not shown), and protective enclosure 168. Handle 162 includes end 152, body 153, and end 154. Light source (not shown) is disposed within end 154. Further, tube 166 and protective enclosure 168 are connected to end 154 of handle 162 via attachment body 164. Tube 166 is preferably conical in shape, approximately, forming a tip at distal end 167.

The glitter can be incorporated into any of a number locations on and/or within hand-holdable light tube 160. For example, the glitter can be disposed within the matrix material forming tube 166, within protective enclosure 168, attached to the major interior and/or major exterior surface of tube 166 and/or protective enclosure 168. and/or present in loose form within tube 166 and/or protective enclosure 168.

In a preferred embodiment, protective enclosure 168 is a diffuse or clear material, such as plastic. Protective enclosure 168 is attached to and extends from end 154 of handle 162 and conforms generally to the shape of, and encloses, tube 166. In one embodiment, protective enclosure 168 is maintained separate from the tube 166. Alternatively, it may also be useful to attach tube 166 to an interior of protective enclosure 168 with an adhesive material.

In one embodiment, tube 166 is adhered (e.g., using an adhesive material) to protective enclosure 168. Suitable adhesive materials may be apparent to those skilled in the art, and include a high bond adhesive (available, for example, in a double-sided tape form from the 3M Company of St. Paul, Minn. under the trade designation "VHB ADHESIVE" (#P9460PC)), an epoxy resin or binder, can also be used. Regardless of the exact form of the adhesive material used to secure the tube to the protective enclosure, the adhesive material is preferably optically clean to minimize the effect, if any, on the light from the light source to the tube of sheet or film material.

Protective enclosure 168 is preferably rigid and serves to protect tube 166 from damage while allowing light from tube 166 to pass there through. Alternatively, protective enclosure 168 may be configured to assume an optical characteristic and filter light produced through tube 166. Protective enclosure 168 also assists in maintaining the extended position of tube 166 relative to handle 162.

As with previous embodiments, hand-holdable toy light tube 160 is preferably activated by rotational movement of end 154 relative to body 153. Light from light source (not shown) is directed into tube 166. Movement of handle 162 imparts a reciprocal movement onto tube 166 and protective enclosure 168. Protective enclosure 168 protects tube 166 from potential damage otherwise presented through accidental contact of hand-holdable toy light tube 160 with an object. Further, protective enclosure 168 maintains tube 166 in an extended position.

Hand-holdable toy light tube 160 optionally includes indicia 165 (which may be, for example, a (U.S.) federally registered trademark) on an outer circumference of protective enclosure 168. Alternatively, for example, indicia 165 may be in the form of a copyright or copyrightable material or in the form of a trademark, including a registered or registrable trademark under any of the laws of the countries, territories, etc. of the world. In another respect, tube 166A can be configured to include optional indicia of a trademark (including a (U.S.) federally registered trademark) and/or copyrightable material as described above.

In another aspect, hand-holdable toy light tube 160 includes optional indicia 169 on the outer circumference of handle 162. Alternatively, another trademark or copyrightable material as described above may be used.

Yet another alternative embodiment of hand-holdable toy light tube according to the present invention is shown in FIGS. 18 and 19. Hand-holdable toy light tube 180 includes handle 182, light source (not shown), glitter according to the present invention (not shown), and tube 184. Handle 182 includes end 186, body 188, and end 190. Light source (not shown) is disposed within end 190 of handle 182, which additionally functions as a switch in a preferred embodiment. Thus, rotational movement of end 190 relative to body 192 controls activation of light source (not shown).

Tube 184 includes first section 192, second section 194, and third section 196. First section 192 is configured to telescopically receive second section 194 and third section 196. In this regard, first section 192 includes proximal end 198, intermediate portion 191 and distal end 193. Similarly, second section 194 includes proximal end 195, intermediate portion 197 and distal end 199. Finally, third section 196 includes proximal end 181, intermediate portion 183 and distal end 185.

The glitter can be incorporated into any of a number locations on and/or within hand-holdable light tube 180. For example, the glitter can be disposed within tube 184 (including one or more sections thereof). attached to the major interior and/or major exterior surface of tube 184 (including such major such of one or more sections thereof), and/or present in loose form within tube 184.

Proximal end 198 of first section 192 is sized for attachment to end 190 of handle 182. Further, intermediate portion 191 of first section 192 is sized to slidably receive second tube 186 in a telescopic fashion. In this regard, intermediate portion 191 of first section 192 preferably assumes a conical shape such that proximal end 198 has a larger diameter than distal end 193. Further, distal end 193 of first section 192 has a diameter slightly smaller than that of proximal end 195 of second section 194. Thus, second section 194 cannot disengage from first section 192 during use.

Second section 194 and third section 196 are constructed similar to first section 192, but with reduced diameters. Thus, second section 194 and third section 196 are preferably conical in shape. Intermediate portion 197 of second section 194 is sized to slidably receive third section 196. However, distal end 199 of second section 194 has a diameter slightly smaller than that of proximal end 181 of third section 196 such that third section 196 does not entirely disengage from second section 194 during use.

With the just described configuration, tube 184 can be maintained in either an extended position, as shown, for example, in FIG. 18, or a retracted position as shown, for example, in FIG. 19. In the extended position, second section 194 extends outwardly from first section 192 such that proximal end 195 of second section 194 is approximately adjacent distal end 193 of first section 192. In this regard, because proximal end 195 of second section 194 has a diameter slightly greater than that of distal end 193 of first section 192, second section 194 is frictionally maintained in the extended position. Third section 196 is similarly maintained in the extended position relative to second section 194. Additional stop or attachment devices may be employed to maintain the tube 184 in the extended position. In the retracted position (FIG. 19), third section 196 and second section 194 slide within first section 192.

In one embodiment, each of first section 192, second section 194, and third section 196 are comprised of a translucent matrix material and glitter according to the present invention. The sheet or film material use for each of first section 192, second section 194, and third section 196 may be the same. or may differ for one or all sections 192–196. For example, the glitter for first section 192 could exhibit a series of optical characteristics (e.g., a series of colors), while glitter for second section 194 and third section 196 exhibits a different series of optical characteristics (e.g., a series of colors). Alternatively, for example, other materials having differing optical characteristics may also be useful for one or two of sections 192, 194, or 196. Additionally, while tube 184 is shown as having three sections 192, 194, 196, a greater or lesser number may also be utilized. Handholdable toy light tube 180 may further include protective enclosure(s) encompassing each of first section 192, second section 194, and/or third section 196, either individually or as a whole.

During use, end 190 of handle 182 is rotated relative to body 188 to activate light source (not shown) via connection to a power supply (not shown). Alternatively, a finger-operated switch may be provided along an outer surface of handle 182. Light from light source is directed from end 190 into tube 184. In the extended position (FIG. 18), at least a portion of tube 184, possibly including first section 192, second section 194, and third section 196, exhibits an optical characteristic(s) (e.g., bright, brilliant colors) in response to light from the light source. Similarly, in the retracted position (FIG. 19), first section 192 exhibits an optical characteristic(s) (e.g., a brilliant, multi-colored optical characteristic).

Hand-holdable toy light tube 180 can be maneuvered from the retracted position (FIG. 19) to the extended position (FIG. 18) by a rapid rotational movement of handle 182. Rotational movement of handle 182 is imparted onto first section 192. Centrifugal force generated by this rotational movement forces second section 194 and third section 196 into the extended position. Alternatively, for example, third section 196 can simply be grasped at distal end 185 by a user and pulled outwardly, thereby extending third section 196 and second section 194. Conversely, tube 184 is maneuvered from the extended position to the retracted position by pushing third section 196 toward handle 182. Once third section 196 is retracted within second section 194, continued force on distal end 199 of second section 194 will retract second and third sections 194, 196 within first section 192.

Use of a telescoping design for the tube enhances user enjoyment by providing a tube extendable, for example, through a simple movement of a user's wrist.

Additional details regarding hand-holdable light tubes can be found, for example, in application having U.S. Ser. No. 09/006,088, filed Jan. 13, 1998.

Figure 20:
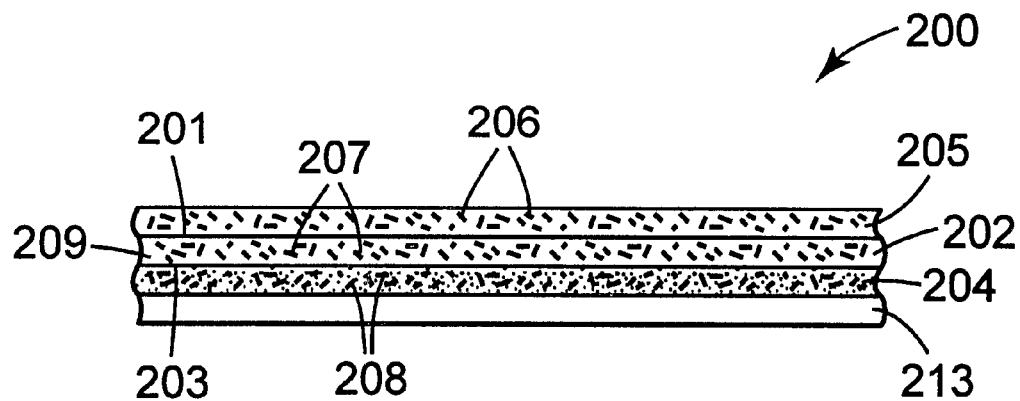
FIG. 20 is a side view in cross-section of a tape according to the present invention.

Referring to FIG. 20, tape 200 comprises sheet material 202, which can be a single or multi-layered material, adhesive material 204 on major surface 203, and at least one of glitter according to the present invention 206, 207, or 208. As shown, glitter 206 is adhered to major surface 201 with (optionally translucent) matrix material 205 (e.g., a binder or adhesive material), glitter 207 is embedded in (optionally translucent) matrix material 209, and glitter 208 is adhered to major surface 203 with adhesive material 211. Glitter 206 can be partially or fully embedded in matrix material 205. If glitter 206 is not present, then matrix material 205 is optional. Optionally, tape 200 further comprises release liner 213. The glitter can be patterned, for example, to provide a design, and/or to be or be a part of, copyrightable material or a trademark (as discussed above, for example, with regard to FIGS. 14–19).

Figure 21:
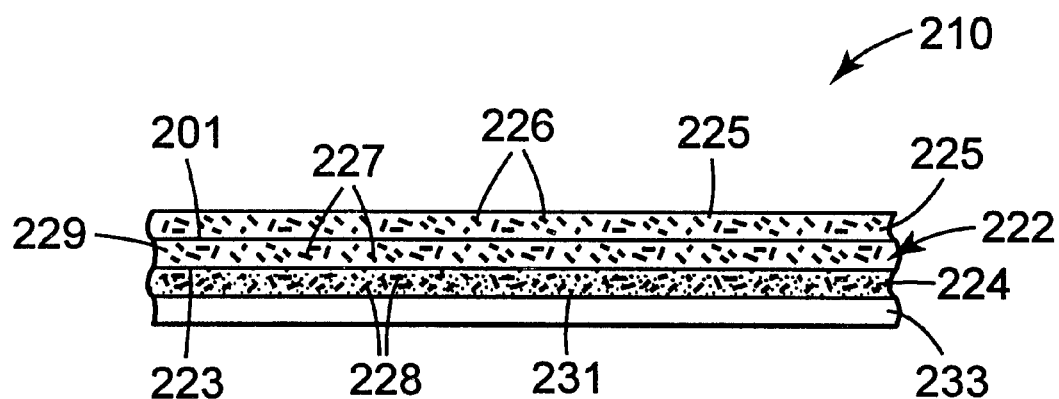
FIG. 21 is a side view in cross-section of a decal according to the present invention.

Referring to FIG. 21, decals (including stickers) 210 comprises sheet material 222, which can be a single or multi-layered material, adhesive material 224 on major surface 223, and at least one of glitter according to the present invention 226, 227, or 228. As shown, glitter 226 is adhered to major surface 201 with (optionally translucent) matrix material 225 (e.g., a binder or adhesive material), glitter 227 is embedded in (optionally translucent) matrix material 229, and glitter 228 is adhered to major surface 203 with adhesive material 23 1. Glitter 226 can be partially or fully embedded in matrix material 225. If glitter 226 is not present, then matrix material 225 is optional. Optionally, decals or stickers 210 further comprises release liner 233. The glitter can be patterned, for example, to provide a design, and/or to be or be a part of, copyrightable material or a trademark (as discussed above, for example, with regard to FIGS. 14–19).

Additional details regarding decals can be found, for example, in copending application having U.S. Ser. No. 09/006,939, filed Jan. 13, 1998 now abandoned.

Figures 22, 22A, 22B, 23:
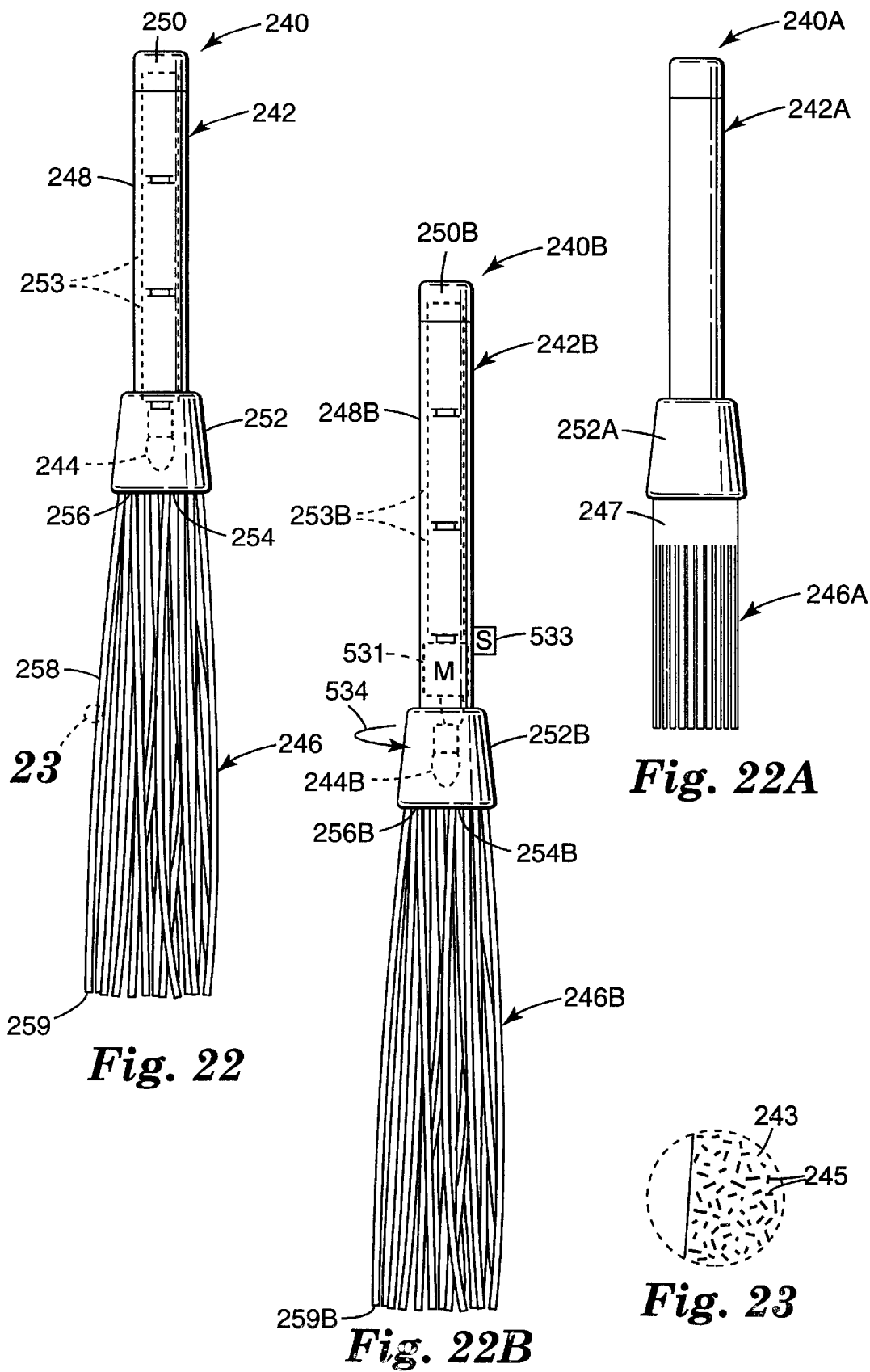
FIG. 22 is a side view of a hand-holdable novelty article according to the present invention.
FIG. 22A is a side view of another hand-holdable novelty article according to the present invention.
FIG. 22B is a side view of another hand-holdable novelty article according to the present invention.
FIG. 23 is a cutaway view of a portion of the hand-holdable novelty article of FIG. 22.

Referring to FIG. 22 illuminating article 210 comprises illuminating surface 224 (illumination provided, for example, by a light source (e.g., an electroluminescent device (e.g., an electroluminescent sheet device), or another light source (e.g., an incandescent light bulb, black light bulb, a halogen light bulb, or a light emitting diode)) and glitter according to the present invention 226 in translucent matrix material 228 (as shown, a binder or adhesive material, although the glitter could be, for example, embedded in the matrix material, or in a sheet material that is adhered or covering the illuminating surface. The glitter can be patterned, for example, to provide a design, and/or to be or be a part of, copyrightable material or a trademark (as discussed above, for example, with regard to FIGS. 14–19).

An "electroluminescent sheet device," which in contrast to a light source (including a light emitting diode), has an extended light emitting surface area (i.e., at least 1 $cm^2$, typically at least 2 $cm^2$, at least 5 $cm^2$, or greater) which typically provides uniform light emission from the surface. Typically, such a device has a length and a width that are much greater than its thickness (i.e., at least 10 times; typically at least 25 times, more typically, at least 100 times, greater than the thickness devices).

Suitable electroluminescent sheet devices (also referred to as "electroluminescent (sheet) lamps") are known in the art, and rely on the electroluminescence of a light emitting material (e.g., phosphor material, organic light emitter (e.g., a triphenyldiamine derivative (TPD), poly phenylene vinylene (PPV), quinolinol metal complex (Al-q), or the like (e.g., Mn-doped ZnS, or alkaline earth thiogallates (e.g., $CaGa_2S_4$,))) in the presence of an electric field, wherein the phosphor (or the like) becomes excited and emits photons. Most of the radiated energy falls within the visible range of the spectrum. Generally, an electroluminescent sheet device is electrically similar to a capacitor and comprises a dielectric layer comprising light-emitting phosphor (or the like) sandwiched between two electrically conductive layers. At least one additional dielectric layer may also be present. The primary purpose of the additional dielectric layer is to allow the electroluminescent material (i.e., the phosphors material or the like) to withstand higher voltages without shorting between the conductive surfaces. Electroluminescent devices illuminate when powered with an applied voltage. As voltage is applied to the conductive surfaces, an electric field is generated across the phosphor (or other material) and dielectric layers. Electrons are excited from the valance band into the conduction band or injected into the conduction band of the luminescent material. Many of these excited electrons decay to lower energy states with the emission of light. Emitted light passes through a transparent front electrode (of the device) as they return to their ground states. Preferably, electroluminescent sheet devices utilized in the practice of the present invention are flat or planer. Typically, electroluminescent sheet devices have a thickness in the range from about 0.05 mm to about 20 mm, more typically, about 0.1 to about 5 mm, depending, for example, on the type of device and substrate.

Generally, there are at least three types of electroluminescent sheet devices, which are sometimes referred to as "organic thin film-type" (small molecule-types (see, e.g., U.S. Pat. Nos. 4,356,429 (Tang), 5,409,783 (Tang) 5,554, 450 (Shi et al.)) and "conjugated polymer-type" (see, e.g., U.S. Pat. No. 5,247,190 (Friend et al.)); "inorganic thin film-type" (see, e.g., U.S. Pat. No. 5,598,059 (Sun et al.)); and inorganic particles (or thick film)-type (see, e.g., U.S. Pat. Nos. 5,469,019 (Mori), 5,508,585 (Butt), 5,156,885 (Budd), 5,418.062 (Budd), 5,439,705 (Budd), 5,491,377 (Janusaukas), and 5,593,782 (Budd)).

Electroluminescent devices can be tailored through the use, for example, of different compositions and/or filters to provide a variety of colors (e.g., violet, blue, blue-green, orange, white, orange-yellow, yellow, and red). Unlike filament or fluorescent lamps. electroluminescent devices do not fail catastrophically or abruptly fail, but rather the brightness of the lamp gradually decreases over long periods of time. The characteristics of the degradation behavior can vary with the different types of electroluminescent devices and materials. Electroluminescent lamp life is typically affected by voltage, frequency, temperature, oxygen, and humidity. Humidity is typically highly detrimental to the luminescent materials in all types of lamps, unless such effect is controlled. Techniques for protecting the lamp material from the effects of humidity are known in the art, and particularly prevalent for the commercially available lamps. Thin film types are generally fabricated on glass substrates, and are protected on the non-light emitting side by metal or other inorganic coatings. Organic types are generally sealed with a second sheet of glass. Thick film particulate type lamps are particularly advantageous because there are currently robust lamps which do not require a glass substrate. Moisture protection is achieved by macroencapsulating the entire lamp structure with sheets of a low permeability polymer (such as that available under the trade designation "ACLAR" from Allied Chemical), or by microencapsulating the particulate phosphor material in a moisture resistant or proof material, such as oxide materials (e.g., titania, alumina, and silica) (see, e.g., U.S. Pat. Nos. 5,156,885 (Budd), 5,418,062 (Budd), 5,439,705 (Budd), and 5,593,782 (Budd)).

Particulate electroluminescent phosphors, for example, are most commonly used in thick film constructions. These devices typically include a layer of an organic dielectric matrix (e.g. polyester, polyethylene terephthalate, cellulosic materials, etc.), preferably having a high dielectric constant, loaded with phosphor particles (e.g., sulfide-based phosphor particles). Such layers are typically coated on a plastic substrate having a transparent front electrode. A rear electrode (e.g., an aluminum foil or screen printed silver ink) is typically applied to the back side of the phosphor layer. When an electric field is applied across the electrodes, the proximate portions of the layer emit light as the phosphor particles therein are excited. Such constructions may further comprise optional dielectric layers between the phosphor layer and rear electrodes.

One preferred electroluminescent (thick film) device comprises, in order, a first electrode, a layer of dielectric matrix loaded with encapsulated electroluminescent phosphor particles, and a rear electrode, wherein the encapsulated phosphor particles each comprise a particle of zinc sulfide-based electroluminescent phosphor which is essentially completely encapsulated within a substantially transparent, continuous metal oxide precursors, and wherein the encapsulated phosphor particles have an initial electroluminescent brightness which is equal to or greater than about 50 percent of the initial electroluminescent brightness of the uncoated phosphor particle. and the percent of electroluminescent brightness retained by the encapsulated phosphor particles following 100 hours operation in an environment having a relative humidity of at least 95 percent is greater that about 70 percent of the intrinsic brightness retained following 100 hours operation, the initial brightness and change in electroluminescent brightness in an environment having a relative humidity of at least 95 percent and intrinsic brightness change being measured under substantially the same operating conditions (for further details, see U.S. Pat. No. 5,593,782 (Budd)).

Preferably, the electroluminescent material (e.g., phosphor) is encapsulated to reduce, minimize, or prevent the effects of moisture or humidity on the life of the device (see, e.g., U.S. Pat. Nos. 5,156,885 (Budd), 5,418,062 (Budd), 5,439,705 (Budd), and 5,593,782 (Budd)). A commercially available phosphor electroluminescent device, which utilizes encapsulated inorganic particles is available, for example, from Durel Corp. of Chandler, Ariz., under the trade designation "DUREL 3 EL".

Other electroluminescent devices which may be suitable in the practice of the present invention are available, for example, form NEC Corporation of Tokyo, Japan and (under the trade designation "PERMA-LIGHT") from Quantex of Rockville, Md.

In one aspect, glitter according to the present invention can be utilized to provide a hand-holdable novelty article comprising a handle (including a first end), and a plurality of sections of a sheet or film material extending for the first end, and a light source (i.e., the article includes a source that generates light as opposed to one that merely reflects ambient light) connected to the handle, wherein the light source is configured to be activated by a power source, and wherein the sheet or film material includes glitter according to the present invention. Preferably, the light source is disposed at the first end of the handle. In another aspect, the light source is preferably a point light source (e.g., a flashlight). When energized or activated, the light source illuminates at least a portion of the plurality of sections of the sheet or film material. Optionally, the article includes a power source electrically coupled to the light source in conjunction with a switch to control activation of the light source.

Referring to FIGS. 22 and 23, exemplary hand-holdable novelty article 240 includes handle 242, light source 244, and plurality of sections of sheet or film material 246. Sheet or film material 246 comprises matrix material (typically a translucent material) 243 and glitter according to the present invention 245. Handle 242 has body 248 and ends 250 and 252. Light source 244 is connected to the handle and is configured to be powered by power source 253 (e.g., battery shown in dashed lines), and is disposed at end 252 of handle 242. Plurality of sections of sheet or film material 246 extend from end 252 of handle 242.

Plurality of sections of sheet or film material 246 can be arranged in a number of different manners. Activation of light source 244 directs light onto at least a portion of glitter 245. Glitter 245 interacts with light from light source 244, producing a visual (e.g., brightly colored) effect.

In one preferred embodiment, hand-holdable novelty article 240 resembles a pom-pon. Body 248 is preferably hollow to maintain power source such as battery 253 for powering light source 244. Further, end 250 is preferably threadably secured to body 248, and end 252 is preferably rotatably secured to body 248.

End 252 is preferably configured to receive and maintain light source 244. Further, end 252 preferably includes translucent or filtered leading edge 254 (e.g., a clear lens) through which light from light source 244 can pass. In this regard, end 252 is configured to direct light from light source 244 to leading edge 254.

In one preferred embodiment, handle 242 is, or is similar to, a flashlight wherein, for example, body 248 and ends 250, 252 can be manufactured separately, but are configured for integral attachment. In this regard, end 250 can be threadably secured to body 248 to maintain power source 253 within body 248. End 252 is preferably rotatably secured to body 248 and acts as a switch operably connected between power source 253 and light source 244. That is, rotation of end 252 relative to body 248 moves light source 244 into and out of contact with power source 253. Alternatively, for example, end 252 can be permanently secured to body 248 and an additional finger-operated switch can be disposed along an outer circumference of body 248 for activating light source 244.

Widths of the sections of sheet or film material can vary as desired, and for many embodiments may range from about 0.2 mm (8 mils) to about 5 mm, typically from about 1.6 mm (0.0625 in.) to about 3 mm (0.125 in.), although other widths may also be useful.

Components of the hand-holdable article can be made of any suitable material, including those disclosed herein, although some materials may be more suitable than others depending on the particular article use. For example, suitable materials for the handle may include rigid material (e.g., hard plastic, aluminum, stainless steel, or wood) or non-rigid materials such as rubber. Preferably, the light source emits visible as described above with regard to FIGS. 14–19.

Preferably, the glitter according to the present invention reflects and transmits light over a wide bandwidth such that when lit, the glitter provides an optical effect such as appearing brightly colored. In one embodiment, the hand-holdable novelty article includes a plurality of sections that do not include glitter according to the present invention (e.g., paper) interspaced with the plurality of sections of sheet or film material that includes the glitter.

Referring to FIG. 22, each of plurality of sections of sheet or film material 246 are preferably each a strand having first, proximal end 256, intermediate portion 258 and second, distal end 259. In one preferred embodiment, plurality of sections of sheet or film material 246 includes at least twenty strands. Proximal end 256 is configured for attachment to end 252 of handle 242. Intermediate portion 258 extends from proximal end 256 and is preferably constructed to be flexible. Distal end 259 is unattached or free. Thus, each of plurality of sections of sheet or film material 246 is configured such that intermediate portion 258 can bend or curve. In one preferred embodiment, the sheet or film material (246) is configured such that when curved, glitter in intermediate portion 258 exhibits at least two different colors (e.g., green in transmission at normal incidence and pink (or magenta) in transmission at oblique angles). That is, at least some glitter in intermediate portion 258 is one color, and others a different (optically discernable) color when viewed from the same location or position. Plurality of sections of sheet or film material 246 are preferably cut from a single sheet of the sheet or film material.

Hand-holdable novelty article 240 of one preferred embodiment can be constructed as follows. Light source 244 is disposed at or near end 252 of handle 242 when light source 244 and handle 242 are a flashlight. Proximal end 256 of each of plurality of sections of sheet or film material 246 is attached to end 252 of handle 242. In one preferred embodiment, each of plurality of sections of sheet or film material 246 is of a similar length. Proximal ends 256 of each of plurality of sections of sheet or film material 246 are attached to end 252 of handle 242 by an adhesive material (e.g., adhesive tape). Alternatively, other ways of attachment are also useful (e.g., a liquid adhesive material).

During use, light source 244 in one preferred embodiment is activated by rotating second end 252 of handle 242 relative to body 248, although other ways of adding light source 244 (e.g., a separate switch) are also useful. Once lit, light from light source 244 is directed through leading edge 254 of handle 242 on to plurality of sections of sheet or film material 246.

The handle of the article according to the present invention can be configured to be held by a user such that movement of the handle, in turn, imparts a motion onto the plurality of sections of sheet or film material, much like a pom-pon. Because distal ends (see, e.g., reference number 259 in FIG. 22) of each of the plurality of sections of the sheet or film material are unattached, the sections of sheet or film material are free to move in all directions. Thus. manipulation of handle results in movement and therefore a perceived change in optical effect (e.g., color) in a plurality of sections of the sheet or film material by a stationary viewer.

Additionally, the handle can be maneuvered by a user to impart a wave-like curve in intermediate portion (see, e.g., reference number 258) of at least one of a plurality of sections of the sheet or film material. The sheet or film material is preferably configured such that when curved, for each viewable glitter particle, an optical characteristic, such as color of an intermediate portion changes. Typically, not all of the plurality of sections of the sheet or film material will curve in the same manner. Therefore, rapid movement of the handle by a user generally creates, particularly in the dark, a brilliant, multi-colored effect, visually resembling a sparkler.

Each of the plurality of sections of the sheet or film material is typically flexible so as to allow curvature over an intermediate portion. However, in some embodiments, each of the plurality of sections of the sheet or film material has a certain amount of rigidity (e.g., sections of sheet or film material 246 will preferably bend, but do not deform on impact). With this configuration, movement of the handle can result in contact between several of plurality of sections of the sheet or film material, producing an audible sound. When the handle is vigorously shaken, numerous contacts can be made, producing a "hissing" sound, closely resembling a burning sparkler. Thus, preferred hand-holdable novelty articles can be similar in both sight and sound to a conventional burning sparkler. Such a and-holdable novelty article does not have the "burning/fire" associated with a conventional sparkler.

The visual appearance of plurality of sections of the glitter can be altered, for example, by including a translucent filter at leading edge of the handle (see, e.g., leading edge 254 of handle 242 in FIG. 22). The filter can alter the wavelengths of the light emitted by the light source varying the color(s) or colors produced by the glitter. Optionally, the filter is or includes a color shifting film or sheet or film material having glitter according to the present invention therein and/or thereon.

In some embodiments according to the present invention (see, e.g., FIG. 22), the plurality of sections of the sheet or film material are attached directly to an end of the handle. Other forms of attachment are also useful. For example, FIG. 22A illustrates an alternative embodiment of a hand-holdable novelty article, which is similar to device 240 shown in FIG. 22. Article 240A includes handle 242A, light source 244A, plurality of sections of sheet or film material 246A, and attachment body 247 for connecting plurality of sections of sheet or film material 246A to end 252A of handle 242A. Although attachment body 252A is shown as a band of a color shifting film integrally formed with plurality of sections of sheet or film material 246A, it may be in other suitable forms such as a conical shell, or a multiply curved shell in the shape of a partial donut. With respect to the form shown, during manufacture, an appropriately sized sheet of the sheet or film material can be cut to provide plurality of sections of sheet or film material 246A. Band 247 can be attached to end 252A of handle 242A, so that plurality of sections of sheet or film material 246A extending therefrom, thus, plurality of sections of sheet or film material 246A and attachment body 252A are thereby integral. Alternatively, for example, attachment body 252A can be an independently manufactured article, such as a strip of material attached at opposite ends to end 252A of handle 242A and plurality of sections of sheet or film material 246A.

Regardless of exact form, attachment body 252A connects plurality of sections of sheet or film material 246A to handle 252A while allowing light from light source 244A to interact with plurality of sections of sheet or film material 246A. In this regard, attachment body 252A can be tubular in form, or may be a solid article configured to allow passage of light from light source 244A.

Motion may be imparted to plurality of sections of sheet or film material 246B using alternative means. Referring to FIG. 22A, one exemplary embodiment of a hand-holdable novelty device according to the present invention (240B) is shown, which is similar to device 240 of FIG. 22, but which employs a mechanism 531 (e.g., a motor as shown) for imparting motion to sheet or film material 246B.

Mechanism 531 is electrically coupled to power source 253B through switch mechanism 533, and mechanically coupled to end 252B. End 252B is rotatably coupled to body 248B. Upon operation of switch mechanism 533, mechanism 531 can be selectively energized for rotation of end 252B relative to body 248B (indicated by rotational arrow 534), about a central axis as defined by longitudinally extending body 248B. Rotation of end 252B at a desired speed will impart a desired amount of motion to sheet or film material 246B. Further, switch mechanism 533 can be used for selective energization of light source 244B.

Figure 24:
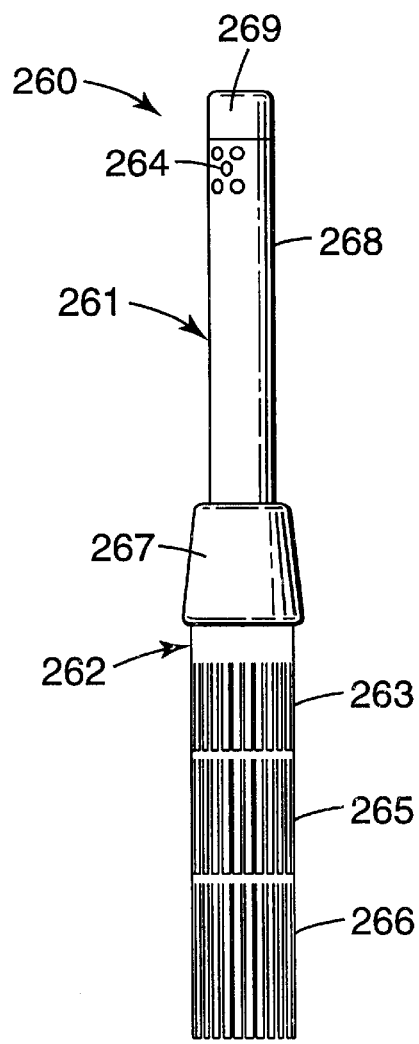
FIG. 24 is a side view of another hand-holdable novelty article according to the present invention.

Another embodiment of a hand-holdable novelty article is shown in FIG. 24. Hand-holdable novelty article 260 includes handle 261, light source (not shown), attachment body 262, first plurality of strands 263, second plurality of strands 265 and third plurality of strands 266. As with previous embodiments, handle 261 includes end 269, body 268 and end 267. Light source (not shown) is disposed within end 267. Further, the first, second and third plurality of strands 263, 265, 266, respectively, are connected to end 267 of handle 261 via attachment body 262.

Each of first, second and third plurality of strands 263, 265, 266 are preferably made of a sheet or film material having glitter according to the present invention therein. However, first, second, and third plurality of strands 263, 265, 266 are of varying lengths. Additionally, first, second and third plurality of strands 263, 265, 266 can be made, for example, of varying types of matrix materials and/or glitter according to the present invention such that during use, a wider variety of colors are displayed.

In addition to providing variable length strands of the sheet or film material, hand-holdable novelty article 260 optionally includes sound device 264 disposed in and/or on handle 261. Sound device 264 is preferably a speaker configured to produce a sound such as a siren. Alternatively, sound device 264 can be or include a radio. Sound device 264 is preferably electrically coupled to power source (not shown) and further enhances the performance of hand-holdable novelty article 260.

Figure 25:
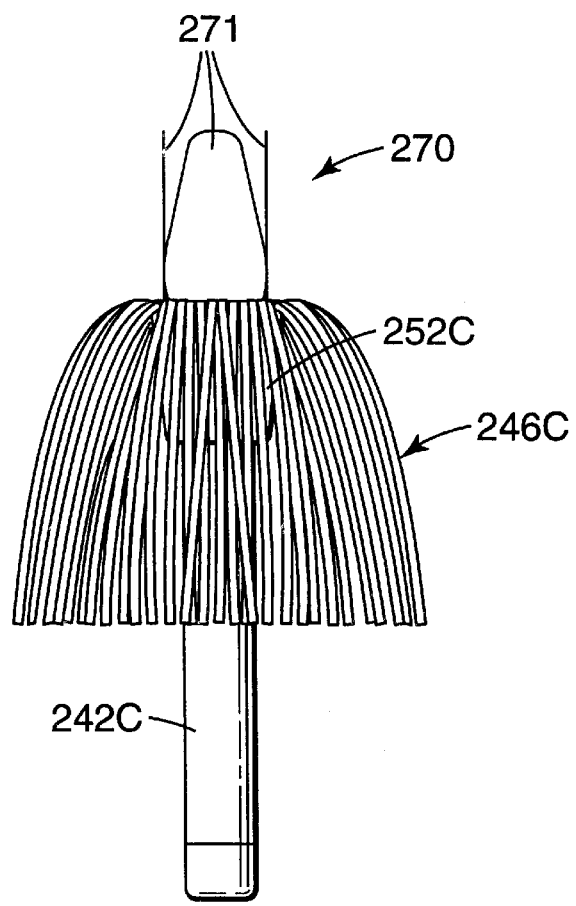
FIG. 25 is a side view of another hand-holdable novelty article according to the present invention.

In yet another embodiment of a hand-holdable novelty article shown in FIG. 25, article 270, which is similar to article 240 shown in FIG. 22, includes handle 242C, light source (not shown), fins 271, and plurality of sections of sheet or film material 246C extending from end 252C of handle 242C. Fins 271 are preferably made of a color shifting film and extend from end 252C of handle 242C. One preferred embodiment includes four fins 271, however, a greater or lesser number can also be used, depending, for example, on the desired effect. Fins 271 are preferably more rigid than plurality of sections of sheet or film material 246C such that when handle 242C is oriented in an upright position (shown in FIG. 25), fins 271 likewise remain upright. Conversely, plurality of sections of sheet or film material 246C are preferably flexible such that they curve downwardly when handle 242C is positioned upright. In the upright position, fins 271 preferably exhibit a candle-like appearance in response to light from a light source (not shown).

While the plurality of sections of sheet or film material has been described as being flexible strands, other forms are also useful. For example, referring to FIG. 26, hand-holdable novelty article 280 has a flower-like appearance. Hand-holdable article 280 includes handle 281, light source 282, and plurality of sections of sheet or film material 283. Sheet or film material 283 comprises matrix material (typically translucent matrix) and glitter according to the present invention.

Handle 281 and light source 282 preferably function similar to handle 242 and light source 244 of FIG. 22. In this regard, handle 281 includes end 284, body 285 having an outer circumference and end 286. Plurality of sections of sheet or film material 283 extend from end 286 of handle 281. End 286 is rotatable relative to body 285 to control activation of light source 282. Alternatively, an external switch can be provided.

In FIG. 26, plurality of sections of sheet or film material 283 are configured to form a flower or flower-like shape. In this regard, each of plurality of sections of sheet or film material 283 is rigid so as to maintain the preferred flower-like shape regardless of handle 281 position or movement. Each of plurality of sections of sheet or film material 283 includes a curved surface to enhance visual appearance in response to light from light source 282 when activated. As such, glitter according to the present invention preferably reflects light from inside the flower-like shape, and reflects light from an outside surface of the flower-like shape. In an alternative embodiment, sections of sheet or film material that does not have glitter according to the present invention therein can be interposed with plurality of sections of sheet or film material 283.

Additionally, hand-holdable novelty article 280 includes optional indicia 287 (which may be, for example, a U.S. federally registered trademark) on outer circumference of handle body 285. Alternatively, the indicia can be in the form of a trademark or copyrighted material (as discussed above, for example, with regard to FIGS. 14–19).

Another embodiment of a hand-holdable novelty article is shown in FIGS. 27A and 27B. As with previous embodiments, hand-holdable novelty article 290 includes handle 291, light source (not shown) and plurality of sections of sheet or film material 292. Sheet or film material 292 comprises matrix material (typically translucent matrix material) and glitter according to the present invention. Handle 291 includes end 296, body 293 and end 294. Light source (not shown) is disposed within end 294 of handle 291, which additionally functions as a switch in the preferred embodiment. Thus, rotational movement of end 294 relative to body 293 controls activation of light source. Further, plurality of sections of sheet or film material 292 are attached to end 294 of handle 291.

Unlike plurality of sections of sheet or film material 246 previously described with reference to FIG. 22, both ends of each of plurality of sections of sheet or film material 292 of FIGS. 27A and 27B are attached to end 294 of handle 291. Further, each of plurality of sections of sheet or film material 292 have an increased width. As shown in FIGS. 27A and 27B, each of plurality of sections of sheet or film material 292 are curved to form a bow. In one preferred embodiment, each of plurality of sections of sheet or film material 292 includes multiple curvatures.

Further, as shown in FIG. 27B, at least one of plurality of sections of sheet or film material 292 includes optional indicia 295 (which can be, for example, a (U.S.) federally registered trademark). Alternatively, the indicia can be in the form of a trademark of copyrightable material (as described above, for example, with regard to FIGS. 14–19). In another respect, plurality of sections of sheet or film material 292 can be configured to assume a shape representative of a trademark (including a federally registered trademark) and/or copyrightable material.

Figure 28:
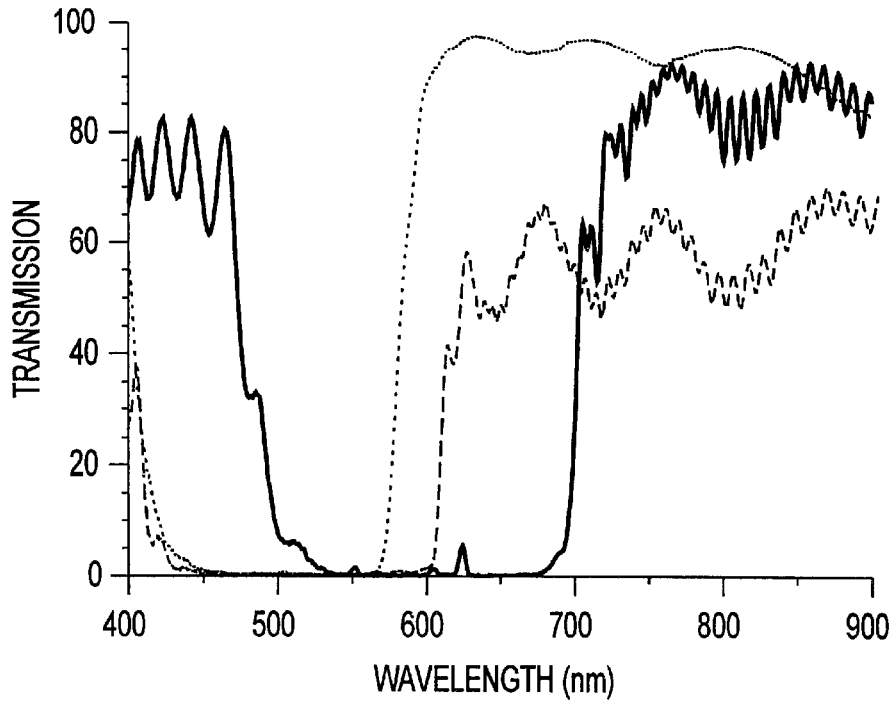
FIGS. 28 and 29 are optical spectra for two color shifting films.

Yet another embodiment of a hand-holdable novelty article according to the present invention is shown in FIG. 28. Hand-holdable novelty article 330 includes handle 332, light source 334, and a plurality of sections of sheet or film material 336. Handle 332 includes end 338, body 340 and end 342. Plurality of sections of sheet or film material 336 are attached to end 338 of handle 332. Unlike previous embodiments, light source 334 is connected to handle 332 near end 342. Light source 334 is thereby connected to handle 332 away from end 338 to which plurality of sections of sheet or film material 336 are attached. Light source 334 is preferably configured to be powered by power source 344 (e.g., battery shown in dashed lines). While the light source is described as being connected to the handle, it is understood that the light source can be connected directly to the handle, or alternatively, connected to the handle via any intermediate structure or elements.

Handle 332 is configured to transmit light from light source 334 to end 338 at which plurality of sections of sheet or film material 336 are attached. Whatever the arrangement, the article is configured so that the light source illuminates at least a portion of the glitter according to the present invention. In this regard, light from light source 334 can be transmitted by, for example, a visible mirror film lining an interior of handle 332. Alternatively, for example, handle 332 can be a light fiber or a light tube. Even further, for example, a portion of handle 332 may include a partially reflective/partially transmissive film that directs some light to plurality of section of sheet or film material 336 and allows some light to pass through the sheet or film material such that the handle 332 appears to be glowing or brightly colored when handle 332 appears is activated. Notably, a device for transmitting light from light source 334 to a region adjacent plurality of section of sheet or film material 336 can be separate from, or integral with, handle 332, or can be simply be the handle itself.

Components of the hand-holdable articles, as well as other articles (including toys) disclosed herein can be made of any of a variety of materials (including those referred to herein). For example, suitable materials may include non-metallic (e.g., rigid or non-rigid polymeric materials) or metallic materials. Other suitable materials may also be apparent to those skilled in the art after reviewing the disclosure of the present invention.

Additional details regarding lighted hand-holdable novelty articles can be found, for example, in application having U.S. Ser. No. 09/006,294, Jan. 13, 1998.

Other uses of glitter according to the present invention, including products utilizing the same, include molding clays or compounds, glue sticks (including hot melt adhesives), liquid glue, architectural foams (e.g. ceiling foams), cosmetics (e.g., fingernail polish, lipstick, eyeliner, facial creams and lotions (including rouge), jewelry (e.g., beads), decorative fountains (e.g., having glitter dispersed in water), kaleidoscopes, sand art (e.g., the glitter mixed with the sand), fishing lures, roofing material (e.g., with the granules on the top surface of roofing shingles), art materials (including art paint), finger paint, crayons (see, e.g., U.S. Pat. No. 5,383,954 (Craig) for additional details regarding incorporating glitter into crayons), puzzle surfaces, board games surfaces, wall coverings, carpet (e.g., included with the conventional carpet fibers), and ribbon (e.g., the glitter can be dispersed within a conventional ribbon material.

More specific examples of products utilizing glitter according to the present invention include molding clays or compounds, such as that commercially available under the trade designations "PLAY-DOH" from Tonka Corp. (Playschool), Inc. of Pawtucket, R.I.). Preferably, the glitter according to the present invention is pretreated with a surfactant (e.g., glycerol) and/or a surfactant is added to the molding compound. The surfactant is preferably miscible with water based molding compounds and is non-toxic. It is believed that use o a surfactant or the like significantly reduces the tendency for the glitter to separate from the molding compound during use. Although not wanting to be bound by any theory, it is believed that the surfactant lowers the surface energy between the polymeric film and the molding compound, resulting in an increase in adhesion between the molding compound and glitter.

Another specific example of a product utilizing glitter according to the present invention are liquid glues (such as that commercially available under the trade designation "ELMER'S GLUE-ALL" from Borden, Inc. of Columbus, Ohio) or hot melt glue sticks having the glitter randomly dispersed therein. Optionally, the product can be provided with different colored glues by tinting or coloring the same, for example, with pigments. A kit could be sold, for example, having two, three, four, or more different tinted or colored glues (e.g., one kit could include three different colored glues, each being one of the primary colors (i.e., red, yellow, and blue)).

Yet another specific example of a product utilizing glitter according to the present invention is decorative or graphic sheeting material. Graphic or decorative sheeting material are used, for example, for signage or vehicle decals. Graphic or decorative sheeting materials typically comprise a thin (i.e., 0.025–0.13 mm (1–5 mil)) sheet of plasticized poly (vinyl chloride) having a layer of acrylic pressure sensitive adhesive on one major surface. Glitter according to the present invention may be added to the poly(vinyl chloride) resin prior to processing the resin into a sheet material. For further details regarding techniques for making such decorative or graphic sheeting materials see, for example, U.S. Pat. No. 4,605,592 (Paquette et al.).

Another specific example of a product utilizing glitter according to the present invention is a three dimensional decorative article, useful, for example, as a paperweight, key chain fob, or emblem. A three dimensional decorative article may be formed, for example, by molding a first thermoformable transparent or translucent (preferably transparent) film to a desired concave shape. Separately, glitter, including glitter according to the present invention. is dispersed in a flowable transparent or translucent polymeric composition. The resulting polymeric composition (i.e., having the glitter dispersed therein) is then poured into a reservoir formed by the concave shape of the first film. The polymeric composition is then solidified by curing or cooling (i.e., for a hot-melt polymeric composition). Optionally, a second film or a reflective substrate may be attached to the polymeric composition either before or after solidification thereof. Primers or tie layers may be used to adhere the polymeric composition to either the first or second films. The decorative article may further comprise an adhesive material on at least a portion of its surface for attachment to a substrate.

Further, with regard to the three dimensional decorative article, the first film may be formed in any known manner such as extrusion, casting from solvent, or casting from an emulsion. Preferably, the film will have suitable elongation and flexibility to be thermoformed into the desired contour. Unoriented films, or films having a low degree of orientation are preferred because they have less internal stress and are less likely to undergo shrinkage than more oriented films, particularly when heated. The first film may be at least partially crosslinked, although crosslinked films may be limited to concave shapes having softer (i.e., less severe) contours. Typically, the first film will range in thickness from about 12 to about 250 micrometers, but films outside of this range may also be useful. Examples of suitable films include plasticized polyvinyl chloride films, polyolefin films, thermoplastic rubber films, acrylonitrile-butadiene styrene/vinyl laminates, and ethylene methylmethacrylic acid copolymer films (commercially available under the trade designation "SURLYN" from E.I. duPont de Nemours and Co.). A suitable polyvinyl chloride film is commercially available, for example, under the trade designation "6669 FILM COAT" from the 3M Company, St. Paul, Minn. The first film may optionally contain other additives such as antioxidants, UV absorbers, UV stabilizers, and reinforcing agents, and may optionally be primed to enhance adhesion to the polymeric composition. Examples of primers include polyvinyl chloride/polyvinyl acetate compositions commercially available, for example, under the trade designations "VAGH" and "VMCH" from Union Carbide, and "DESMOLAC 4125" from Mobay Chemical Co.

The polymeric composition of the three dimensional decorative article may be any of the polymeric matrix materials described hereinabove. A preferred polymeric composition is a transparent or translucent thermosetting polyurethane. Polyurethanes are the reaction product of one or more polyols with an isocyanate curative, typically in the presence of a catalyst. Polyurethanes are preferred because of their durability, impact resistance, environmental stability, as well as their resistance to degradation from exposure to cleaning solvents, gasoline, water and the like. When using a polyurethane, the glitter particles are typically mixed with the polyol component, which is then mixed with a stochiometric amount of an aliphatic polyisocyanate (e.g., the aliphatic polyisocyanate commercially available, for example, under the trade designation "DESMODUR N-3300" from Mobay Chemical Co.). In some applications, it is desirable to use a soft, flexible polyurethane, characterized by having a Shore D hardness of about 45 to 65 (preferably about 45 to 55). A soft, flexible polyurethane may be formed, for example, by reacting an aliphatic diisocyanate-polyproplyenetriol adduct with a mixture of a polyester glycol and low to medium molecular weight polypropylenetriols. Other suitable polyurethanes are commercially available, for example, under the trade designations "DESMODUR" and "BAYTEC" from Mobay Chemical Co., "URALITE" from Hexcel Corp., and "CONATHANE" from Conap, Inc. Suitable polyurethanes are also commercially available, for example, from Inolex Chemical Co., and Dexter Plastics.

In one method for making the three dimensional decorative article, the first thermoformable film is placed over a mold (preferably a porous mold), heated, and then formed into a concave shape by using pressure or vacuum to draw the film into contact with the mold. The glitter particles are dispersed in a polyol, and the resulting dispersion is mixed with an isocyanate curative to form a reactive polyurethane composition. The resulting composition, which preferably has a Brookfield viscosity between about 3000 to 5000 cps for ease of handling, is then poured into the thermoformed first film and is cured. The second film may be placed over the polymeric composition either before or after curing of the composition. When the film is adhered after curing, an adhesive material (e.g. a pressure-sensitive adhesive) may be used to adhere the film to the cured polymeric composition.

In another embodiment of a three dimensional decorative article the second film is placed over the composition before curing and the reactive polyurethane composition bonds to the second film. Preferably, the second film is a reflective film. Suitable reflective films include color shifting film and visible mirror film described above, as well as metallized (i.e., aluminum or silver vapor coated) polyester films, and chrome plated flexible films. Alternatively, for example, the second film may be a mirror or a chrome plated sheet. The resulting decorative article has unique appearance resulting from light reflecting and refracting from the reflective surface of the second film to the highly reflective glitter particles according to the present invention.

The three dimensional decorative article may further include a layer of adhesive material to attach it to another substrate such as a window, plaque or trophy, automobile, clothing, or jewelry. Suitable adhesive materials for such use are known in the art and include acrylic pressure-sensitive adhesives, silicone pressure-sensitive adhesives, tackified block copolymer pressure-sensitive adhesives, epoxy adhesives, silicone adhesives, and the like. Acrylic pressure-sensitive adhesives are preferred because of the variety of surfaces to which they adhere. Examples of suitable acrylic pressure-sensitive adhesives include those described in U.S. Pat. Nos. Re 24,906 (Ulrich), 4,181,752 (Martens et al.), 4,329,384 (Vesley et al.), 4,710,536 (Klingen et al.), 4,415,615 (Esmay et al.), and 5,086,088 (Kitano, et al.).

Another specific example of a product utilizing glitter according to the present invention are tracks (e.g. racetracks) for toy cars, such as that available from Mattel, Inc. of El Segundo, Calif. under the trade designation "HOT WHEELS" having glitter according to the present invention therein.

It is also within the scope of the present invention to combine glitter according to the present invention with conventional glitter, as well as the glitter disclosed in application having U.S. Ser. No. 09/006,291, filed Jan. 13, 1998 now abandoned.

The first three examples that follow illustrate exemplary embodiments of the manufacture of exemplary color shifting films or visible mirror films for use in the present invention. Particular materials and amounts thereof recited in these examples, as well as other conditions and details, should not be construed to unduly limit this invention. All parts and percentages are by weight unless otherwise indicated.

EXAMPLE 1

The following example illustrates the preparation of a color shifting film.

A co-extruded film containing 209 layers was made on a sequential flat-film making line via a co-extrusion process. This multilayer polymer film was made from polyethylene naphthalate (PEN) and polymethyl methacrylate (PMMA CP82) where PEN was the outer layers or "skin" layers. A feedblock method (such as that described by U.S. Pat. No. 3,801,429) was used to generate about 209 layers which were co-extruded onto a water chilled casting wheel and continuously oriented by conventional sequential length orienter (LO) and tenter equipment. PEN with an intrinsic viscosity (IV) of 0.56 dl/g (60 wt. % phenol/40 wt. % dichlorobenzene) was delivered to the feedblock by one extruder at a rate of 60.5 kg/hr and the PMMA was delivered by another extruder at a rate of 63.2 Kg/hr. These melt streams were directed to the feedblock to create the PEN and PMMA optical layers. The feedblock created 209 alternating layers of PEN and PMMA with the two outside layers of PEN serving as the protective boundary layers (PBL's) through the feedblock. The PMMA melt process equipment was maintained at about 249° C.; the PEN melt process equipment was maintained at about 290° C.; and the feedblock, skin-layer modules, and die were also maintained at about 290° C.

An approximately linear gradient in layer thickness was designed for the feedblock for each material, with the ratio of thickest to thinnest layers being about 1.72:1. This hardware design of first-to-last layer thickness ratio of 1.73:1 was too great to make the bandwidth desired for the colored mirror of this example. In addition, a sloping blue band edge resulted from the as-designed hardware. To correct these problems, a temperature profile was applied to the feedblock. Selected layers created by the feedblock can be made thicker or thinner by warming or cooling the section of the feedblock where they are created. This technique was required to produce an acceptable sharp band edge on the blue side of the reflection band. The portion of the feedblock making the thinnest layers was heated to 304° C., while the portion making the thickest layers was heated to 274° C. Portions intermediate were heated between these temperature extremes. The overall effect is a much narrower layer thickness distribution which results in a narrower reflectance spectrum.

After the feedblock, a third extruder delivered a 50/50 blend of 0.56 dl/g IV and 0.48 dl/g IV PEN as skin layers (same thickness on both sides of the optical layer stream) at about 37.3 Kg/hr. By this method, the skin layers were of a lower viscosity than the optics layers, resulting in a stable laminar melt flow of the co-extruded layers. Then the material stream passed through a film die and onto a water cooled casting wheel using an inlet water temperature of about 7° C. A high voltage pinning system was used to pin the extrudate to the casting wheel. The pinning wire was about 0.17 mm thick and a voltage of about 5.5 kV was applied. The pinning wire was positioned manually by an operator about 3–5 mm from the web at the point of contact to the casting wheel to obtain a smooth appearance to the cast web.

The cast web was length oriented with a draw ratio of about 3.8:1 at about 130° C. In the tenter, the film was preheated before drawing to about 138° C. in about 9 seconds and then drawn in the transverse direction at about 140° C. to a draw ratio of about 5:1, at a rate of about 60% per second. The finished film had a final thickness of about 0.02 mm.

The optical spectra for the film of this example are shown in FIG. 28. The film exhibited blue in transmission at normal incidence; yellow in reflection at normal incidence; red in transmission at oblique angles; and cyan in reflection at oblique angles.

EXAMPLE 2

The following example illustrates the preparation of a another color shifting film.

A multilayer film containing about 418 layers was made on a sequential flat-film making line via a co-extrusion process. This multilayer polymer film was made PET and polyester resin (available under the trade designation "ECDEL 9967" from Eastman Chemical Co. of Rochester, N.Y.) where PET was the outer layers or "skin" layers. A feedblock method (such as that described by U.S. Pat. No. 3,801,429) was used to generate about 209 layers with an approximately linear layer thickness gradient from layer to layer through the extrudate.

The PET, with an Intrinsic Viscosity (IV) of 0.56 dl/g was pumped to the feedblock at a rate of about 34.5 Kg/hr and the polyester resin ("ECDEL 9967") at about 41 Kg/hr. After the feedblock, the same PET extruder delivered PET as protective boundary layers (PBL's ), to both sides of the extrudate at about 6.8 Kg/hr total flow. The material stream then passed though an asymmetric two times multiplier (U.S. Pat. Nos. 5,094,788 and 5,094,793) with a multiplier ratio of about 1.40. The multiplier ratio is defined as the average layer thickness of layers produced in the major conduit divided by the average layer thickness of layers in the minor conduit. This multiplier ratio was chosen so as to leave a spectral gap between the two reflectance bands created by the two sets of 209 layers. Each set of 209 layers has the approximate layer thickness profile created by the feedblock, with overall thickness scale factors determined by the multiplier and film extrusion rates.

The melt process equipment for the polyester resin ("ECDEL 9967") was maintained at about 250° C., the PET (optics layers) melt process equipment was maintained at about 265° C., and the feedblock, multiplier, skin-layer melt stream, and die were maintained at about 274° C.

The feedblock used to make the film for this example was designed to give a linear layer thickness distribution with a 1.3:1 ratio of thickest to thinnest layers under isothermal conditions. To achieve a smaller ratio for this example, a thermal profile was applied to the feedblock. The portion of the feedblock making the thinnest layers was heated to 285° C., while the portion making the thickest layers was heated to 265° C. In this manner the thinnest layers are made thicker than with isothermal feedblock operation, and the thickest layers are made thinner than under isothermal operation. Portions intermediate were set to follow a linear temperature profile between these two extremes. The overall effect is a narrower layer thickness distribution which results in a narrower reflectance spectrum. Some layer thickness errors are introduced by the multipliers, and account for the minor differences in the spectral features of each reflectance band. The casting wheel speed was adjusted for precise control of final film thickness, and therefore, final color.

After the multiplier, a thick symmetric PBL (skin layers) was added at about 28 Kg/hour that was fed from a third extruder. Then the material stream passed through a film die and onto a water cooled casting wheel. The inlet water temperature on the casting wheel was about 7° C. A high voltage pinning system was used to pin the extrudate to the casting wheel. The pinning wire was about 0.17 mm thick and a voltage of about 5.5 kV was applied. The pinning wire was positioned manually by an operator about 3–5 mm from the web at the point of contact to the casting wheel to obtain a smooth appearance to the cast web. The cast web was continuously oriented by conventional sequential length orienter (LO) and tenter equipment. The web was length oriented to a draw ratio of about 3.3 at about 100° C. The film was preheated to about 100° C. in about 22 seconds in the tenter and drawn in the transverse direction to a draw ratio of about 3.5 at a rate of about 20% per second. The finished film had a final thickness of about 0.05 mm.

Figure 29:
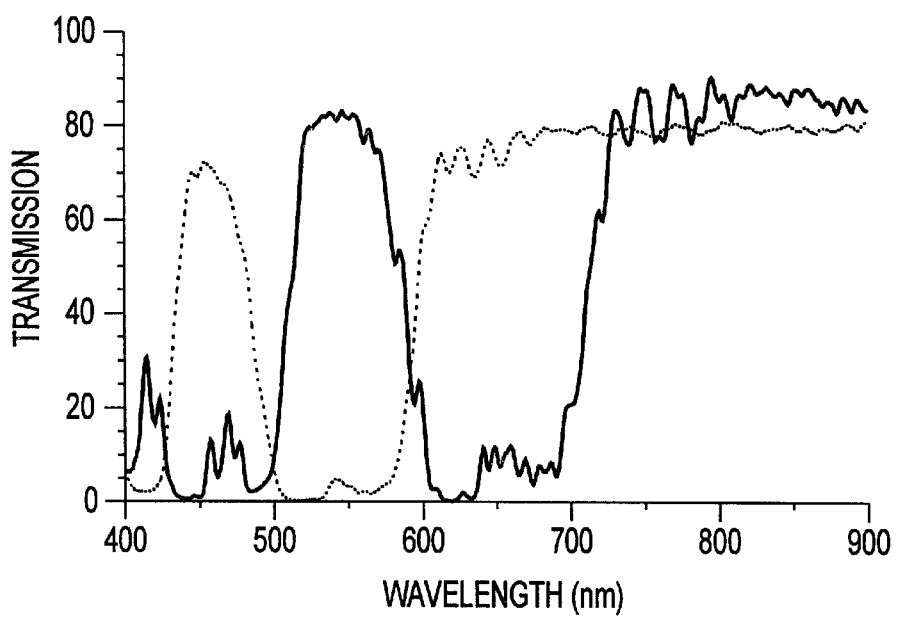

The optical spectra for the film of this example are shown in FIG. 29. The film exhibited green in transmission at normal incidence; magenta in reflection at normal incidence; magenta in transmission at oblique angles; and green in reflection at oblique angles.

It is to be noted that many different colors can be, for example, produced by modifying one or more parameters of the procedures described in Examples 1–2. Thus, for example. within certain limitations, the speed of the casting wheel can be adjusted to result in relative thickening or thinning of the optical layers within the extruded web. This results in a shift of the reflectance band to a different wavelength, which changes the color of the resulting film at a given angle of incidence.

EXAMPLE 3

A coextruded film containing 601 layers was made on a sequential flat-filmmaking line via a coextrusion process. A polyethylene naphthalate (PEN) with an intrinsic viscosity of 0.57 dl/g (60 wt %% phenol/40 wt % dichlorobenzene) was delivered by extruder A at a rate of 114 pounds per hour with 64 pounds per hour going to the feedblock and the rest going to skin layers described below. PMMA (CP-82 from ICI of Americas) was delivered by extruder B at a rate of 61 pounds per hour with all of it going to the feedblock. PEN was on skin layers of the feedblock. The feedblock method was used to generate 151 layers using the feedblock such as those described in U.S. Pat. No. 3,801,429, after the feedblock two symmetric skin were coextruded using extruder C metering about 30 pounds per hour of the same type of PEN delivered by extruder A. This extrudate passed through two multipliers producing an extrudate of about 601 layers. U.S. Pat. No. 3,565,985 describes similar coextrusion multipliers. The extrudate passed through another device that coextruded skin layers at a total rate of 50 pounds per hour of PEN from extruder A. The web was length oriented to draw ratio of about 3.2 with the web temperature at about 280° F. The film was subsequently preheated to about 310° F. in about 38 seconds and drawn in the transverse direction to a draw ratio of about 4.5 at a rate of about 11% per second. The film was then heat-set at 440° F. with no relaxation allowed. The finished film thickness was about 3 mil.

The following examples illustrate the incorporation of glitter according to the present invention into molding compounds.

EXAMPLE A

A 0.051 mm (2 mil) visible mirror film was converted by Glitterex Corporation, Belleville, N.J. into 0.38 mm (15 mil) hexagonal shaped glitter particles. About 0.6 gram of ACS grade glycerol ($C_3H_8O_3$) (commercially available from EM Science, Gibbstown, N.J.) was added to about 2.4 grams of the glitter. The glycerol was mixed with the glitter using a metal spatula until the surface of the glitter particles were coated with glycerol and the mixture had a uniform appearance. Next, about 66 grams of orange colored molding compound (commercially available under the trade designation "PLAY-DOH" from Tonka Corp. (Playschool), Inc. of Pawtucket, R.I.) was added to the glitter/glycerol mixture. The molding compound, glitter, and glycerol were then stirred together using a metal spatula to form a mixture having a uniform appearance.

The resulting molding compound was held over a sheet of white paper and manipulated/worked by hand (i.e., stretched, twisted) to simulate in-use conditions. The paper served to collect and to provide a contrasting background for any glitter particles dislodged from the molding compound during this test. It was observed that the glitter particles remained in the molding compound with few glitter particles collecting on the white paper.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. Glitter particles comprising film comprising a plurality of alternating layers of at least a first and second polymeric material, wherein at least one of the first or second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05.

2. The glitter particles according to claim 1 wherein at least a portion of said glitter particles comprised of said film have particle sizes less than about 10 mm.

3. The glitter particles according to claim 1 wherein said glitter particles comprised of said film have particle sizes in the range from about 50 micrometers to about 3 mm.

4. The glitter particles according to claim 1 wherein at least a portion of said glitter particles comprised of said film have a shape selected from the group consisting of a circle, a square, a rectangle, a triangle, a diamond, a star, an alphanumeric, and mixtures thereof.

5. The glitter particles according to claim 1 wherein at least a portion of said glitter particles comprised of said film include irregularly shaped particles.

6. The glitter particles according to claim 1 wherein at least a portion of said glitter particles comprised of said film include an abrasion resistant coating.

7. The glitter particles according to claim 1 wherein at least a portion of said glitter particles comprised of said film include an anti-static coating.

8. The glitter particles according to claim 1 wherein at least a portion of said glitter particles comprised of said film include an ultra-violet light-absorbing coating.

9. The glitter particles according to claim 1 wherein at least a portion of said glitter particles comprised of said film include an adhesive material.

10. The glitter particles according to claim 1 wherein said glitter particles comprised of said film have particle sizes less than 3 mm.

11. The glitter particles according to claim 1 wherein said glitter particles comprised of said film have particle sizes in the range from about 50 micrometers to about 3 mm.

12. The glitter particles according to claim 1 wherein said glitter particles comprised of said film are in loose form.

13. The glitter particles according to claim 1 wherein said film has a thickness less than about 125 micrometers.

14. The glitter particles according to claim 1 wherein said film has a thickness in the range from about 15 micrometers to about 50 micrometers.

15. An article comprising a substrate having glitter particles attached to a surface of said substrate, said glitter particles comprising film comprising a plurality of alternating layers of at least a first and second polymeric material, wherein at least one of the first or second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05.

16. The article according to claim 15 wherein at least a portion of said glitter particles comprised of said film have particle sizes less than 10 mm.

17. The article according to claim 16 wherein at least a portion of said glitter particles are randomly oriented on said substrate surface.

18. A composite article comprising glitter particles dispersed within a translucent matrix material, said glitter particles comprising film comprising a plurality of alternating layers of at least a first and second polymeric material, wherein at least one of the first and second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05.

19. The composite article according to claim 18 wherein at least a portion of said glitter particles comprising said film have a particle sizes less than 10 mm.

20. The composite article according to claim 19 wherein said matrix is transparent.

21. The composite article according to claim 19 wherein said matrix material comprises at least one cured polymer selected from the group consisting of acrylics, polyurethanes, and vinyls.

22. The composite article according to claim 18 further comprising a pigment.

23. The composite article according to claim 18 wherein said glitter particles are non-uniformly distributed throughout said matrix material.

24. A composite article comprising glitter particles dispersed within a matrix material, said glitter particles comprising film comprising a plurality of alternating layers of at least a first and second polymeric material, wherein at least one of the first or second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05, and wherein at least a portion of said glitter comprising said film is observable by a viewer of said article.

25. A dispersion comprising liquid medium and glitter particles, said glitter particles comprising film comprising a plurality of alternating layers of at least a first and second polymeric material, wherein at least one of the first or second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05.

26. A dispersible combination comprising liquid medium and glitter particles, said glitter particles comprising film comprising a plurality of alternating layers of at least a first and second polymeric material, wherein at least one of the first or second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05.

27. The dispersion according to claim 26 wherein at least a portion of said glitter particles comprised of said film have a particle sizes less than 10 mm.

28. The dispersion according to claim 27 further comprising binder precursor material.

29. The dispersion according to claim 28 which is finger nail polish.

30. The dispersion according to claim 28 which is paint.

31. The dispersion according to claim 27 further comprising curable binder material.

32. The dispersion according to claim 27 wherein said liquid medium includes water.

33. A molding compound comprising glitter particles dispersed therein, said glitter particles comprising film comprising a plurality of alternating layers of at least a first and second polymeric material, wherein at least one of the first or second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05.

34. An injection moldable composition comprising glitter particles dispersed within an injection moldable polymer material, wherein said glitter particles comprise film comprising a plurality of alternating layers of at least a first and second polymeric material, wherein at least one of the first or second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05.

35. The injection moldable composition according to claim 34 wherein said polymer material is in the form of pellets.

36. A composition, comprising:

a substrate;

a matrix disposed on said substrate; and a plurality of glitter particles disposed in said matrix wherein said glitter particles comprise film comprising a plurality of alternating layers of at least a first and second polymeric material, wherein at least one of the first or second polymeric materials is birefringent, and wherein the difference in indices of refraction of the first and second polymeric materials for visible light polarized along both mutually orthogonal in-plane axes of the film is at least 0.05, and wherein the difference in indices of refraction of the first and second polymeric materials for visible light polarized along a third axis normal to the plane of the film is less than about 0.05.

37. A cosmetic composition comprising the glitter of claim 1, said cosmetic composition being adapted for application to the hair or skin.

38. A cosmetic composition according to claim 37, said cosmetic composition being a powder adapted for application to the hair or skin.

39. A cosmetic composition according to claim 37, said cosmetic composition being a liquid adapted for application to the hair or skin.

40. A cosmetic composition according to claim 37, said cosmetic composition being a cream adapted for application to the hair or skin.

41. A cosmetic composition according to claim 37, said cosmetic composition being a semi-solid adapted for application to the hair or skin.

42. A cosmetic composition according to claim 37, said cosmetic composition being a gel adapted for application to the hair or skin.

43. A cosmetic composition comprising the glitter of claim 1, said cosmetic composition being selected from the group consisting of hair spray, hair gel, hair mousse, lipstick, lipgloss, face powder, liquid cosmetic foundation, body paint, body powder, fingernail polish, eyeshadow, eyeliner, mascara, cosmetics that may be applied to the teeth, moustache wax, rouge and massage oil.

44. A topical medicament composition comprising the glitter of claim 1, said topical medicament composition being adapted for application to the hair or skin.

45. The topical medicament composition of claim 44, said composition comprising an anti-itching medicament.

46. The topical medicament composition of claim 44 said composition comprising a topical pain relief medicament.

47. A composition comprising the glitter of claim 1, said composition being adapted for application to the hair or skin, said composition being a suncreen composition comprising at least one UV absorbing component.

* * * * *

UNITED STATES PATENT AND TRADEMARK OFFICE
CERTIFICATE OF CORRECTION

PATENT NO. : 6,455,140 B1
DATED : September 24, 2002
INVENTOR(S) : Whitney, Leland R.

It is certified that error appears in the above-identified patent and that said Letters Patent is hereby corrected as shown below:

Title page,
Item [56], References Cited, U.S. PATENT DOCUMENTS, ",540,765" should read -- 0,540,768 --

Column 1,
Line 42, delete the word "spinkled" and insert in place thereof -- sprinkled --

Column 3,
Line 34, delete "tot he" and insert in place thereof -- to the --

Column 6,
Line 30, delete "." following "polymer"

Column 8,
Line 62, delete "." following "dimethyl"

Column 11,
Line 11, delete "800.000." and insert in place thereof -- 800,000. --

Column 18,
Line 60, delete "." following "and"

Column 19,
Line 34, delete "." following "dispersed"
Line 38, insert "." following "therein"

UNITED STATES PATENT AND TRADEMARK OFFICE
CERTIFICATE OF CORRECTION

PATENT NO. : 6,455,140 B1
DATED : September 24, 2002
INVENTOR(S) : Whitney, Leland R.

It is certified that error appears in the above-identified patent and that said Letters Patent is hereby corrected as shown below:

Column 20,
Line 19, insert "." following "106"

Column 25,
Line 52, delete "." following the word "same" and insert in place thereof -- , --

Column 26,
Line 57, delete "23 1." and insert in place thereof -- 231. --

Signed and Sealed this

Thirteenth Day of July, 2004

JON W. DUDAS
*Acting Director of the United States Patent and Trademark Office*